(12) United States Patent
Ezerzer et al.

(10) Patent No.: US 11,207,381 B2
(45) Date of Patent: *Dec. 28, 2021

(54) CYTOKINE RECEPTOR PEPTIDES, COMPOSITIONS THEREOF AND METHODS THEREOF

(71) Applicant: SYMTHERA CANADA LTD., Toronto (CA)

(72) Inventors: Chai Ezerzer, Nes Ziona (IL); Nicholas Harris, Rehovot (IL)

(73) Assignee: SYMYTHERA CANADA LTD., Ontario (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/895,699

(22) Filed: Feb. 13, 2018

(65) Prior Publication Data
US 2019/0022185 A1 Jan. 24, 2019

Related U.S. Application Data

(60) Continuation of application No. 15/236,829, filed on Aug. 15, 2016, now Pat. No. 9,931,376, which is a division of application No. 14/257,447, filed on Apr. 21, 2014, now Pat. No. 9,416,158, which is a division of application No. 12/225,122, filed as application No. PCT/IL2007/000350 on Mar. 18, 2007, now Pat. No. 8,703,911.

(60) Provisional application No. 60/782,689, filed on Mar. 16, 2006.

(51) Int. Cl.
| | |
|---|---|
| *A61K 38/00* | (2006.01) |
| *C07K 14/00* | (2006.01) |
| *A61K 38/19* | (2006.01) |
| *A61K 38/20* | (2006.01) |
| *C07K 14/715* | (2006.01) |
| *A61K 38/17* | (2006.01) |
| *C07K 7/06* | (2006.01) |
| *A61K 9/00* | (2006.01) |

(52) U.S. Cl.
CPC .......... *A61K 38/195* (2013.01); *A61K 9/0019* (2013.01); *A61K 38/177* (2013.01); *A61K 38/1793* (2013.01); *A61K 38/19* (2013.01); *A61K 38/2053* (2013.01); *C07K 7/06* (2013.01); *C07K 14/7158* (2013.01); *A61K 38/00* (2013.01)

(58) Field of Classification Search
None
See application file for complete search history.

(56) References Cited

U.S. PATENT DOCUMENTS

| | | |
|---|---|---|
| 6,087,115 A | 7/2000 | Gershbngorn et al. |
| 6,132,987 A | 10/2000 | Charo et al. |
| 7,105,488 B1 | 9/2006 | Tarasova et al. |
| 7,259,000 B2 | 8/2007 | Dinchuk et al. |
| 2003/0003440 A1 | 1/2003 | Lopalco |
| 2003/0186889 A1 | 10/2003 | Forssmann |

FOREIGN PATENT DOCUMENTS

| | | |
|---|---|---|
| WO | 9811218 | 3/1998 |
| WO | 9943711 | 9/1999 |
| WO | 0018431 | 4/2000 |
| WO | 0114886 | 3/2001 |
| WO | 0142277 | 6/2001 |
| WO | 2004104041 | 12/2004 |
| WO | 2006010138 | 1/2006 |
| WO | 2007105224 | 9/2007 |

OTHER PUBLICATIONS

Elsner J. et al., "Chernokine receptor antagonists: a novel therapeutic approach in allergic diseases", Allergy, vol. 59, Dec. 2004, pp. 1243-1258, XP002443740.
Zlotnik A. et al., "Chernokines: A new classification system and their role in immunity", Immunity, Cell Press, U.S. vol. 12, Feb. 2000, pp. 121-127 X00022206441SSN: 1074-7613.
Bowie et al., 1990, Science 247: 1306-1310.
Wells, 1990, Biochemistry 29:8509-8517.
NGO et al., 1994, The Protein Folding Problem and Tertiary Structure Prediction, Merz, et al., eds, Birkhauser, Boston, pp. 433-506.
Wang et al., 2001, J. Biol. Chem. 276:49213-49220.
Opal et al., 2000, Chest. 117: 1162-1172.
Su et al., 2012, Journal of Biomedicine and Biotech, Article ED 347141.
Dinarello, 2000, Chest 118:503-508.
Scitable, Essentials of Cell Biology, Unit 4.2, http://www.nature.com/scitable/nated/topicpage/gper-14047472, downloaded Jul. 20, 2015.
Murdoch et al., 2000, Blood 95:3032-3043.

*Primary Examiner* — Elizabeth C. Kemmerer
*Assistant Examiner* — Regina M DeBerry
(74) *Attorney, Agent, or Firm* — Pillsbury Winthrop Shaw Pittman, LLP

(57) ABSTRACT

The invention provides a pharmaceutical composition including a peptide comprising at least a portion of a chemokine receptor or a G-protein coupled receptor and optionally a cytokine. The pharmaceutical composition of the invention may be used for altering immune system functioning, for example, to treat an immune system disorder, such as an autoimmune disease, multiple sclerosis, transplant rejection, psoriasis and asthma. The invention also provides peptides that may be used in the pharmaceutical composition and a method for preparing the pharmaceutical composition of the invention. The invention further provides a method for to treating an immune system disorder, such as an autoimmune disease, multiple sclerosis, transplant rejection, and psoriasis asthma.

13 Claims, 19 Drawing Sheets
Specification includes a Sequence Listing.

CYTOKINE RECEPTOR PEPTIDES, COMPOSITIONS THEREOF AND METHODS THEREOF

CROSS-REFERENCE TO EARLIER APPLICATIONS

This application is a continuation of U.S. application Ser. No. 15/236,829, filed Aug. 15, 2016, which is a divisional of U.S. application Ser. No. 14/257,447, filed Apr. 21, 2014, now U.S. Pat. No. 9,416,158, which is a divisional of U.S. application Ser. No. 12/225,122, filed Sep. 8, 2009, now U.S. Pat. No. 8,703,911, which is a National Phase Application filed under 35 U.S.C. 371 as a national stage of PCT/IL2007/000350, filed Mar. 18, 2007, and application claiming the benefit under 35 U.S.C. 119(e) of U.S. Provisional Application No. 60/782,689, filed Mar. 16, 2006, each of the above applications being hereby expressly incorporated by reference in its entirety and each being assigned to the assignee hereof.

FIELD OF THE INVENTION

This invention relates to peptides which bind cytokines and their use in immune disorders.

BACKGROUND OF THE INVENTION

The following publications are considered relevant for an understanding of the invention.

Anders, H. J., Frink, M., Linde, Y., Banas, B., Wornle, M., Cohen, CD., Vielhauer, V., Nelson, P. J., Grone, H. J. and Schlondorff, D. (2003) CC chemokine ligand 5/RANTES chemokine antagonists aggravate glomerulonephritis despite reduction of glomerular leukocyte infiltration. J Immunol 170, 5658-66.

Attwood, M., Borkakoti, N., Bottomley, G., Conway, E., Cowan, I., Fallowfield, A., Handa, B., Jones, P., Keech, E., Kirtland, S., Williams, G. and 15 Wilson, F. (1996) Identification and characterisation of an inhibitor of interleukin-8: a receptor based approach. Bioorganic & Medicinal Chemistry Letters 6, 1869-74.

Attwood, M., Conway, E., Dunsdon, R., Greening, J., Handa, B., Jones, P., Jordan, S., Keech, E. and Wilson, F. (1997) Peptide based inhibitors of 20 interleukin-8: structural simplification and enhanced potency. Bioorganic & Medicinal Chemistry Letters 7, 429-32.

Blanpain, C., Migeotte, I., Lee, B., Vakili, J., Doranz, B. J., Govaerts, C., Vassart, G., Doms, R. W. and Parmentier, M. (1999) CCR5 binds multiple CCchemokines: MCP-3 acts as a natural antagonist. Blood 94, 1899-905.

Bruhl, H., Cihak, J., Schneider, M. A., Plachy, J., Rupp, T., Wenzel, I., Shakarami, M., Milz, S., Ellwart, J. W., Stangassinger, M., Schlondorff, D. and Mack, M. (2004) Dual role of CCR2 during initiation and progression of collagen-induced arthritis: evidence for regulatory activity of CCR2+ T cells. J Immunol 172, 890-8.

Christen, U. and von Herrath, M. G. (2004) Manipulating the type 1 vs type 2 balance in type 1 diabetes. Immunol Res 30, 309-25.

Cox, M. A., Jenh, C. H., Gonsiorek, W., Fine, J., Narula, S. K., Zavodny, P. J. and Hipkin, R. W. (2001) Human interferon-inducible 10-kDa protein and human interferon-inducible T cell alpha chemoattractant are allotopic ligands for human CXCR3: differential binding to receptor states. Mol Pharmacol 59, 707-15.

Dogan, R. N. and Karpus, W. J. (2004) Chemokines and chemokine receptors in autoimmune encephalomyelitis as a model for central nervous system inflammatory disease regulation. Front Biosci 9, 1500-5.

Ferreira, A. M., Rollins, B. J., Faunce, D. E., Burns, A. L., Zhu, X. and Dipietro, L. A. (2005) The effect of MCP-1 depletion on chemokine and chemokine-related gene expression: evidence for a complex network in acute inflammation. Cytokine 30, 64-71.

Fulkerson, P. C., Zimmermann, N., Brandt, E. B., Muntel, E. E., Doepker, M. P., Kavanaugh, J. L., Mishra, A., Witte, D. P., Zhang, H., Farber, J. M., Yang, M., Foster, P. S. and Rothenberg, M. E. (2004) Negative regulation of eosinophil recruitment to the lung by the chemokine monokine induced by TEN-gamma (Mig, CXCL9). Proc Natl Acad Sci USA 101, 1987-92.

Gaupp, S., Pitt, D., Kuziel, W. A., Cannella, B. and Raine, C. S. (2003) Experimental autoimmune encephalomyelitis (EAE) in CCR2(-/-) mice: susceptibility in multiple strains. Am J Pathol 162, 139-50.

Gayle, R. B., 3rd, Sleath, P. R., Srinivason, S., Birks, C. W., Weerawarna, K. S., Cerretti, D. P., Kozlosky, C. J., Nelson, N., Vanden Bos, T. and Beckmann, M. P. (1993) Importance of the amino terminus of the interleukin-8 receptor in ligand interactions. J Biol Chem 268, 7283-9.

Gerard, C. and Rollins, B. J. (2001) Chemokines and disease. Nat Immunol 2, 108-15.

Godessart, N. and Kunkel, S. L. (2001) Chemokines in autoimmune disease. Curr Opin Immunol 13, 670-5.

Horuk, R. (2003) Development and evaluation of pharmacological agents targeting chemokine receptors. Methods 29, 369-75.

Kim, M. Y., Byeon, C. W., Hong, K. H., Han, K. H. and Jeong, S. (2005) Inhibition of the angiogenesis by the MCP-1 (monocyte chemoattractant protein-1) binding peptide. FEBS Lett 579, 1597-601.

Loetscher, P., Pellegrino, A., Gong, J. H., Matadi, I., Loetscher, M., Bardi, G., Baggiolini, M. and Clark-Lewis, I. (2001) The ligands of CXC chemokine receptor 3, I-TAC, Mig, and IP 10, are natural antagonists for CCR3. J Biol Chem 276, 2986-91.

Mackay, C. R. (2001) Chemokines: immunology's high impact factors. Nat Immunol 2, 95-101.

Nakajima, H., Sugino, M., Kimura, F., Hanafusa, T., Ikemoto, T. and Shimizu, A. (2004) Decreased CD14+ CCR2+ monocytes in active multiple sclerosis. Neurosci Lett 363, 187-9.

Ogilvie, P., Bardi, G., Clark-Lewis, I., Baggiolini, M. and Uguccioni, M. (2001) Eotaxin is a natural antagonist for CCR2 and an agonist for CCR5. Blood 97, 1920-4.

Onuffer, J. J. and Horuk, R. (2002) Chemokines, chemokine receptors and small-molecule antagonists: recent developments. Trends Pharmacol Sci 23, 459-67.

Petkovic, V., Moghini, C., Paoletti, S., Uguccioni, M. and Gerber, B. (2004a) Eotaxin-3/CCL26 is a natural antagonist for CC chemokine receptors 1 and 5. A human chemokine with a regulatory role. J Biol Chem 279, 23357-63.

Petkovic, V., Moghini, C., Paoletti, S., Uguccioni, M. and Gerber, B. (2004b) I-TAC/CXCL11 is a natural antagonist for CCR5. J Leukoc Biol 76, 701-8.

Proudfoot, A. E., Power, C. A., Rommel, C. and Wells, T. N. (2003) Strategies for chemokine antagonists as therapeutics. Semin Immunol 15, 57-65.

Quinones, M. P., Ahuja, S. K., Jimenez, F., Schaefer, J., Garavito, E., Rao, A., Chenaux, G., Reddick, R. L., Kuziel, W. A. and Ahuja, S. S. (2004) Experimental arthritis in CC chemokine receptor 2-null mice closely mimics severe human rheumatoid arthritis. J Clin Invest 113, 856-66.

Rossi, D. and Zlotnik, A. (2000) The biology of chemokines and their receptors. Annu Rev Immunol 18, 217-42.

Sabroe, I., Peck, M. J., Van Keulen, B. J., Jorritsma, A., Simmons, G., Clapham, P. R., Williams, T. J. and Pease, J. E. (2000) A small molecule antagonist of chemokine receptors CCR1 and CCR3. Potent inhibition of eosinophil function and CCR3-mediated HIV-1 entry. J Biol Chem 275, 2598592.

Schwarz, M. K. and Wells, T. N. (2002) New therapeutics that modulate chemokine networks. Nat Rev Drug Discov 1, 347-58.

Szekanecz, Z., Kim, J. and Koch, A. E. (2003) Chemokines and chemokine receptors in rheumatoid arthritis. Semin Immunol 15, 15-21.

Thomas, M. S., Kunkel, S. L. and Lukacs, N. W. (2002) Differential role of IFN-gamma-inducible protein 10 kDa in a cockroach antigen-induced model of allergic airway hyperreactivity: systemic versus local effects. J Immunol 169, 7045-53.

Thomas, M. S., Kunkel, S. L. and Lukacs, N. W. (2004) Regulation of cockroach antigen-induced allergic airway hyperreactivity by the CXCR3 ligand CXCL9. J Immunol 173, 615-23.

Wells, T. N., Power, C. A., Shaw, J. P. and Proudfoot, A. E. (2006) Chemokine blockers—therapeutics in the making? Trends Pharmacol Sci 27, 417.

Xanthou, G., Duchesnes, C. E., Williams, T. J. and Pease, J. E. (2003) CCR3 functional responses are regulated by both CXCR3 and its ligands CXCL9, CXCL10 and CXCL11. Eur J Immunol 33, 2241-50.

Zlotnik, A. and Yoshie, 0. (2000) Chemokines: a new classification system and their role in immunity. Immunity 12, 121-7.

Chemokines in Health and Disease

The immune system promotes health by combating foreign pathogens, alleviating intrinsic disease and repairing physical injury. Infected, injured, or otherwise compromised tissues mobilize cells of the immune system by releasing chemo-attractants called chemokines (CKs) into the blood stream. The same CKs induce the activation of leukocytes and direct the differentiation of lymphocytes [Rossi, 2000; Zlotnik, 2000]. The deployment of immune cells is essential, not only to confront pathogenic challenge, but also for immune surveillance and tolerance to "self" [Mackay, 2001]. Close to fifty different human CKs and twenty CK receptors (CKRs) respond to multifarious pathogens and disease states. Tight regulatory control of the CK system imparts rapid, measured and apposite responses to the various pathogenic challenges. Of equal importance to health is the control which prevents the immune system from acting against "self". An immune response which is inappropriate, excessive, or protracted, relative to the pathogenic insult, if any, will cause injury to healthy tissue. Such aberrant immune responses are responsible for the clinical conditions of multiple sclerosis, inflammatory bowel disease (Crohn's disease, ulcerative colitis), rheumatoid arthritis, psoriasis, asthma and juvenile diabetes, the major and prevalent autoimmune diseases. Experimental studies with animal models of disease [Gerard, 2001; Dogan, 2004; Szekanecz, 2003] and clinical observations [Gerard, 2001; Godessart, 2001] indicated that the levels of CKs and their cognate receptors correlate with specific autoimmune diseases.

Current Treatment of Autoimmune Disease

The etiology of no single autoimmune disease is known, but disease pathology, in every case, is the result of immune cell activity directed against "self". It follows, therefore, that the "state of the art" treatment is restricted to the induction and maintenance of disease remission. Multiple sclerosis (MS), the most common cause of neurological disability in young adults, presents with a relapsing-remitting course and is followed by a secondary progressive phase. Steroids are the first choice of treatment to shorten the duration of relapse and accelerate recovery. Long term treatment, with Non Steroidal Anti Inflammatory Drugs (NSAIDs), is given to maintain, or extend remission. Inflammatory bowel disease (IBD) affects over 1 million Americans today. Manifested by severe abdominal pain and diarrhea, it is associated with an increased risk of bowel cancer. For patients suffering mild IBD, remission is induced with NSAIDs. Because of the adverse side effects of steroids, they are reserved for patients with moderate to severe disease and for those who do not respond to NSAIDs. When the disease is refractory to steroids, immunosuppressant drugs are used.

Established and new treatments of autoimmunity act by modulating and if necessary, suppressing the immune system. Both approaches run the risk of side effects, the short term of which are known, the long term, which cannot always be predicted. The shortcomings of steroids, the first line of treatment for severe MS and IBD are well documented: gastrointestinal, dermatologic, neurological, endocrinological, ophthalmic and metabolic side effects. Remission in MS is "extended" by interferon beta and glatiramer acetate (Copaxone), but drug efficacy, tantamount to a 30% reduction in the frequency of relapse, is offset by severe side effects, such as fatigue, pain and bladder dysfunction. The range of medications extending remission in IBD is wider, but the side effects no less severe. NSIADs are intolerable to a significant number of IBD patients and the alternatives, the immuno-suppressants 5-AZT and 6-mp, cause severe side effects. Prolonged use of a new generation of antibody drugs, exemplified by Remicade, is beginning to reveal a negative side. Remicade has been linked with tuberculosis, opportunistic infection and the activation of latent MS (Centocor, Inc. 2005). Add to this deteriorating safety profile the high cost and administration by intravenous infusion and this innovative treatment becomes a less than an attractive alternative to tried and tested medications. There is a need for improved medication to treat acute inflammation in disease relapse and provide long term treatment to maintain remission.

Chernokine Receptors (CKRs) as Conventional Drug Targets

The CKR, a member of the G-protein Coupled Receptor (GPCR) family, has a drug target pedigree. More than forty five percent of all marketed drugs target GPCRs [Horuk, 2003]. Given that the ligands of GPCRs are low molecular weight peptides (histamine, dopamine, serotonin), it was predicted that CKRs would be tractable targets for small molecule drugs (Proudfoot et al., 2003). The majority of drug candidates targeting CKRs, including those under development and those which have been abandoned, are indeed small molecule inhibitors [Wells, 2006]. Based on steric and energetic considerations [Onuffer, 2002] and empirical studies [Sabroe, 2000], it was proposed that small molecule antagonists of CKRs should be non-competitive inhibitors of CKs that block ligand-receptor interaction by stabilizing the receptor in an inactive conformation.

CKRs are known to interact with both their cognate and with unrelated CK ligands, a phenomenon known as "redundancy". As a functional definition of CK-CKR interaction, a "cognate" CKR-CK pair is defined as a CKR and a CK for which the CKR is activated by nanograms of the CK to induce intracellular signaling (calcium mobilization, kinase and lipase activation). With respect to the same CK-CKR system, an "unrelated" CKR-CK combination is defined as a CKR which requires at least three orders of magnitude more of CK, micrograms, to elicit a positive, negative, or unproductive intracellular response.

The identity of CKRs as GPCRs is an evident advantage for drug development. The atypical involvement of these GPCRs in physiological immunity, however, makes CKRs equivocal drug targets and even a therapeutic liability. Antibodies against the receptor, CCR2, which is expressed by inflammatory T cells and monocytes, were used to treat experimental collagen-induced arthritis [Bruhl, 2004]. The treatment was therapeutic during disease initiation (day 0-15), but deleterious in disease progression (day 21-36). It transpired that a sub-population of regulatory T cells, responsible for immune tolerance, is expanded several fold during the phase of disease progression. The antibodies, by blocking the CCR2 receptors of regulatory T cells, exacerbated disease symptoms Inhibition of the same drug target expressed by different cell types, CCR2 in the example, can be therapeutic, or pathologic, depending on the function of the cell expressing the targeted CKR. The CK, RANTES/CCL5* (*CK classification: [Zlotnik, 2000]) and its cognate receptor, CCR5, are examples of disease-related proteins that are also essential for physiological immunity. Elevated levels of CCL5 and CCR5 correlated with glomerular cell proliferation and macrophage infiltration in experimental glomerulonephritis. CK analogues (Met-RANTES and amino-oxypentane-RANTES), which block the receptor, reduced glomerular cell proliferation and macrophage infiltration, but aggravated clinical symptoms [Anders, 2003]. The CK analogues were observed to be therapeutic antagonists of leukocyte recruitment, but pathogenic activators of resident macrophages. CKRs, validated GPCR drug targets, are potential therapeutic liabilities as mediators of physiological immunity.

CKs and CKRs constitute a network of interacting proteins [Schwarz, 2002]. Drugs directed at individual proteins of a network risk perturbing the network as a whole. It follows, therefore, that when interacting and interdependent proteins of the network are essential for physiological immunity, targeting one of the proteins may affect the overall function of the immune system and so reduce the drug's efficacy. CK gene knock-out has been the preferred experimental approach to study the physiological consequences of CK network interference. In a comparative study of inflammatory cells from MCP1/CCL2 null mice and their wild type counterparts, it was found that eliminating MCP-1/CCL2 altered immune responses to disease [Ferreira, 2005]. Equivalent tissues and cells from null and wild-type diseased mice showed significant differences in their respective CK and CK receptor profiles. Network principles were also observed in tissues derived from the MCP-1/CCL2 null mice. Reconstituted expression of MCP-1/CCL2 in macrophages of the CK knock-out mice selectively suppressed the expression of CKs, those specifically induced by MCP-1/CCL2 inactivation. Physiological immunity in genetically altered animals, as in their wild type counterparts, was dictated by principles of network responses and adaptation.

In experimental animal models of disease, the relevance of networking is most conspicuous at the cellular level. Experimental autoimmune encephalomyelitis (EAE), a rodent model of multiple sclerosis, was used to study the role of CCR2 in disease development [Gaupp, 2003]. The recruitment of monocytes and macrophages into the CNS was examined in CCR2 knock-out, disease-induced mice. Contrary to what was expected, inactivation of CCR2 did not confer resistance to EAE in the mice. CNS lesions did contain diminished levels of monocytes, proof of impaired monocyte function, but also elevated levels of neutrophils. CK (IL-8/CXCL8) and CK receptor (CCR1, CCR5) profiles of the experimental mice were found to be consistent with augmented neutrophil levels in the lesions. It was proposed that the CK-CKR network of the CCR2 null mice responded to disease induction with a "compensatory" immune response involving alternative immune regulator molecules and effector cells. The foregoing example is yet another expression of the network principle. Neutralization of a disease-related protein, one which is important for physiological processes in general, can elicit a counter response, which itself can be pathological. A murine model of experimental arthritis, which reproduces the symptoms of severe human rheumatoid arthritis, provided another illustration of the physiological consequences of network interference [Quinones, 2004]. CCR2 knock-out mice were used to study the role of the receptor in experimental arthritis. The CKR is implicated in disease pathogenesis, therefore, it was not anticipated that the phenotype of the CCR2 knock-out mice would be similar to that found in severe human arthritis, elevated T cell levels and monocytes and macrophages concentrated in the inflamed joints. The proffered explanation was that disease in the CKR compromised mice stimulated the expression of alternative CKRs to mobilize the inflammatory cells. The consequence of perturbing a physiologically essential network, even for therapeutic effect, can be to elicit compensatory reactions to consolidate, but potentially exacerbate, the status quo.

The CK-CKR axis, despite the "druggable" attributes of GPCRs and their small molecule ligands, is demonstrably problematic as a drug target. It functions as a network of interactive and interdependent regulatory proteins central to physiological immunity. Compensatory and possibly deleterious responses may therefore be the unavoidable consequences of pharmacological intervention in the network.

The Chemokine—Chemokine Receptor Network

A disproportionate number of chemokine (CK) ligands, ill-defined ligand specificity and equivocal CK functionality in vitro, were cited as proof of CK "redundancy" and worse still, "promiscuity". Such epithets, although consistent with data at the time, were incompatible with a CK—Chemokine Receptor (CKR) network essential for physiological immunity and pathological autoimmunity. Re-examination of the original data, in the light of subsequent functional studies and structure-activity analyses, reveals physiological relevance in both the ligand to receptor ratio and ostensibly indiscriminate receptor activation. To begin with, CKs, which are agonists of their cognate receptors, were found to be natural antagonists of unrelated receptors, as determined by chemotaxis and $Ca^{2+}$ flux assays. Three agonists of the receptor, CXCR3, MIG/CXCL9, IP10/CXCL10 and I-TAC/CXCL-11, were shown to be antagonists of the unrelated receptor, CCR3 [Loetscher, 2001]. The most potent of the three, I-TAC/CXCL11, was found to be a natural antagonist of CCR5 [Petkovic, 2004]. Eotaxin/CCL11, an agonist of CCR3, was also shown to be an agonist and natural antagonist of the unrelated receptors CCR5 and CCR2, respectively [Ogilvie, 2001]. Another cognate ligand and agonist of CCR3, Eotaxin3/CCL26, was found to be a natural antagonist of unrelated receptors CCR1 and CCR5 [Petkovic, 2004]. MCP3/CCL7, a cognate agonist of receptors CCR1, 2 and 3, was shown to be a natural antagonist of the receptor, CCR5 [Blanpain, 1999]. The concomitant activation and inhibition of CKRs was interpreted to be a mechanism for regulating the recruitment of functionally discrete sub-populations of leukocytes. To illustrate the point, MIG/CXCL9 and Eotaxin/CCL11, by altering the balance between Th1 and Th2 cells, could determine the course of Allergic Airway Inflammation [Thomas, 2004; Fulkerson, 2004]. MIG/CXCL9 is an agonist of CXCR3, expressed by Th1 cells and an antagonist of CCR3, expressed by Th2 cells. Eotaxin/CCL11, a cognate ligand of CCR3, was also shown to have a high affinity binding site in the unrelated receptor, CXCR3 [Xanthou, 2003]. A refinement of the point, activation/inhibition of CKRs, was regulation of T cell recruitment by differential activation of the same receptor [Thomas, 2002].

IP-10/CXCL10 and MIG/CXCL9, cognate ligands of CXCR3, could respectively enhance, or diminish eosinophil accumulation and airway hyper-reactivity. Cumulative data now show that the disease-related distribution and activities of immune cells are in fact a corollary of CK multiplicity and specificity for diverse CKRs.

Since neither experimental data, nor clinical evidence distinguishes between wild type and disease-related CKs, it is presumably the same chemo attractants that mobilize the immune cells of physiological and pathological immune responses. CK pathogenicity appears to be the consequence of inordinate, inappropriate and enduring wild-type CK activity, phenomena consistent with CK network deregulation. CK to receptor binding analyses were carried out to elucidate the molecular bases for the regulation of CK-CKR interactions. MIG/CXCL9 and IP-10/CXCL10 bind competitively the receptor CXCR3 but non-competitively with respect to the third related CK, ITAC/CXCL11 [Cox, 2001]. In this example, functionally related CKs were shown to interact with discrete and overlapping sites in their cognate receptor. The anomalous activities of CKs, those of CKs interacting with unrelated receptors, may be more informative about CK network regulation per se. For example, the cognate ligands of CXCR3 inhibited CCR3 functional responses and were observed to displace that receptor's cognate ligand, Eotaxin/CCL11 [Loetscher, 2001]. A more detailed study of the same system disclosed that ITAC/CXCL11, cognate ligand of CXCR3, efficiently displaced Eotaxin/CCL11 from the extra-cellular loops of the latter's receptor, CCR3. Cognate and unrelated ligands, therefore, can share overlapping binding sites within the same receptor [Xanthou, 2003]. Another anomalous, but informative observation, concerns Eotaxin/CCL11 and its unrelated receptor, CXCR3. Although Eotaxin/CCL11 is neither an agonist, nor an antagonist of CXCR3 in vitro, the receptor has a high-affinity binding site for this CK which can be competitively occupied by ITAC/CXCL11 [Xanthou, 2003].

Chemokines as Innovative Drug Targets

An upshot of the molecular structure-activity analyses and binding studies is that receptors comprise CK binding sequences that, given the context, are regulators of CK activity. In the context of the CKR, regulatory elements are potential, but problematic drug targets, because the receptors are essential for physiological immunity.

Functional studies and complementary molecular analyses of CK receptors, have disclosed regulatory sequences in the receptors of physiological and disease-related CKs. Anomalous interactions of CKs with unrelated receptors implicate ubiquitous cryptic regulatory sequences important for general CK-CKR network activity. CKR derived CBPs, capable of modifying CK binding activities, are not without precedent. In a study to identify and define receptor sequences responsible for IL-8/CXCL8 and GRO-α/CXCL1 binding, receptor-derived sequences were shown to be competitive inhibitors of CK binding [Gayle, 1993]. A peptide derived from an extra-cellular domain of the same receptor, CXCR1, was found to be an antagonist of the cognate CK, IL8/CXCL8 [Attwood, 1996] and when chemically modified, the peptide was made a stronger inhibitor [Attwood, 1997]. More recently, an MCP1/CCL2 binding peptide, homologous to a sequence in an extra-cellular loop of the CKRs CCR2 and CCR3, was shown to be angiostatic by antagonizing MCP-1/CCL2 binding to CCR2 [Kiln, 2005].

Mechanism of Drug Action—Redress of Immune Imbalance

The pathogenesis of all autoimmune diseases is patently de-regulated and dysfunctional immune activity. A challenge for any therapeutic approach is to manipulate immune processes that, in the same individual, both cause clinical symptoms and protect against disease. To date, no therapy has met the challenge satisfactorily. Autoimmune diseases are treated with low efficacy drugs which cause significant side effects. Most of the current drugs are small synthetic molecules whose deficiencies appear to derive from their mechanism of action, irreversible inhibition of disease related proteins.

Drug candidates targeting CKRs belong to the class of small synthetic molecules [Wells, 2006]. Following from the preceding discussion, drugs of this type are inherently flawed. None can be expected to block and neutralize a CKR with impunity, given the organization of CKs and their receptors as a network which is essential for physiological immunity. The principles of network activity govern immune responses at the molecular and cellular levels and dictate the outcome, therapeutic, or deleterious, of inhibitory drug activity. The overriding objective of the network is to maintain immune balance, any perturbation of the network eliciting a response to redress the balance. Experimental models of autoimmune disease and clinical evidence provide manifold examples of network activity where disease manifests itself as immune imbalance and health is restored by redressing the balance. Take, for example, allergen challenge in the lung, which elicits deleterious eosinophils and protective Th1 lymphocytes [Fulkerson, 2004; Thomas, 2002]. Allergen-induced CK, Eotaxin/CCL11, recruits inflammatory eosinophils. At the same time, Th1 cells express the CK, MIG/CXCL9, a natural inhibitor of eosinophils. The inference was that the inflammatory status of the allergic lung was dictated by competition between positive and negative regulatory CKs, the result of which competition was translated into a balance between Th1 and eosinophilic cells. The clinical symptoms of type 1 diabetes, herpes stromal keratitis and multiple sclerosis, are infection, tipping of the T helper (Th) lymphocyte balance in favor of a type 1 milieu [Christen, 2004]. Support for the hypothesis was provided by the diabetogenic RIP-LCMV mouse model. Type 1 CKs and cytokines were shown to be responsible for the diabetic state of the RIP-LCMV mouse. It was suggested, with qualification, that redressing the immune imbalance by inhibiting the type 1 inducing factors, or administering Type 2 cytokines, could be therapeutic. Immune balance is argued to be a salient determinant of disease progression in relapsing-remitting multiple sclerosis [Nakajima, 2004]. Levels of Th1-related CKs are elevated in the active phase of MS whereas MCP-1/CCL2, reported to induce Th2 reactions, is elevated in remission. An analysis of blood from patients with active MS revealed elevated levels of Th1 lymphocytes and significantly reduced levels of monocytes expressing CCR2, the cognate receptor of MCP-1/CCL2. The results were interpreted as evidence that elevated MCP1/CCL2 and a subset of peripheral monocytes expressing CCR2, may correct the Th1/Th2 imbalance to create conditions for disease remission.

The Th1-Th2 dichotomy influences immune balance in physiological immunity and is a determining factor in causing the immune imbalance that is characteristic of autoimmune disease. Under prevailing physiological conditions, Th1 and Th2-like cells are in equilibrium, contributing to the establishment and maintenance of immune balance. Innate and extraneous stimuli induce Th1 and Th2-like immune responses that create new, transient equilibria and immune imbalance. Responses that entail modification of the immune cell repertoire establish a new Th1-Th2 equilibrium, restoring immune balance. In autoimmune disease, a loss of tolerance is expressed as pathological Th1-Th2 disequilibrium and immune imbalance. In the absence of treatment, resolution of the Th1-Th2 disequilibrium is transient and an enduring immune imbalance leads to relapse. Effective treatment of an autoimmune disease, therefore, must restore Th1-Th2 cell equilibrium to redress the immune imbalance for tolerance and disease remission. It follows, therefore, that one way to treat autoimmune disease is to alter the pathogenic equilibrium state. A pharmacological intervention is required to create a new equilibrium and to redress immune imbalance for tolerance. Its application must be incremental and in keeping with the principles of equilibrium dynamics for maximal therapeutic effect and minimal, detrimental side effects.

A recurrent theme in the study of autoimmune disease is the intercalation of physiological immunity with pathological autoimmunity. Evidence has been presented to show that the former state is achieved when immune regulators and effectors are in balance and the latter, disease state, when they are in imbalance. Given that the balance is contingent on a network of regulatory proteins, negation of a protein, albeit disease related, portends imbalance. Efficacy, therefore, must be sought in a drug which modulates and does not negate the disease-related activity of the network-associated protein.

SUMMARY OF THE INVENTION

The present invention is based on the novel and unexpected finding that a combination consisting of a chemokine and at least a fragment of a chemokine receptor protein is capable of affecting immune system functioning. The inventors have found that a combination consisting of a chemokine and at least a fragment of a chemokine receptor can affect immune system function in a way that is different from the effect observed when the chemokine or at least, a fragment of the chemokine receptor is administered alone. The pharmaceutical composition of the invention may be used to alter immune system functioning, and thus to treat immune system diseases.

Thus, in its first aspect, the present invention provides a pharmaceutical composition comprising:
  (a) A cytokine;
  (b) A peptide comprising at least a portion of a cytokine receptor or aG-protein coupled receptor (GPCR); and
  (c) A physiologically acceptable carrier. The cytokine may be a chemokine.

If the receptor may is a cytokine receptor it may be a chemokine receptor.

In a preferred embodiment, the peptide of the pharmaceutical composition comprises at least a portion of an extracellular domain of the receptor. In an even more preferred embodiment, the peptide of the pharmaceutical composition comprises at least a portion of a regulatory sequence of the receptor. The pharmaceutical composition may include a cytokine that, in the absence of the at least a portion of the receptor, is an inflammatory chemokine, a constitutive chemokine or a dual function chemokine. The peptide may bind to the chemokine.

For example, the chemokine MIG, is expressed at elevated levels in inflammatory conditions and is classified as an inflammatory CK. The peptide WVFGNAMCK (SEQ ID NO. 5), referred to herein as "Peptide 8" is a fragment of the ECL-2 of human C—C chemokine receptor type 2 (CCR2; Monocyte Chemoattractant Protein 1 receptor). As demonstrated below, Peptide 8 has a pro-inflammatory effect when administered alone to disease-induced mice, increasing inflammation by. 44% compared with disease-induced, untreated animals. However, quite unexpectedly, a combination of MIG and Peptide 8 has an anti-inflammatory effect when administered to disease-induced animals.

As another example, the chemokine RANTES when administered alone to disease induced mice is pro-inflammatory, and Peptide 8 has a pro-inflammatory effect when administered alone to disease-induced mice. However, a combination of RANTES and Peptide 8 when administered together to disease-induced mice has an anti-inflammatory effect.

While not wishing to be bound by a particular theory, it is believed that when the cytokine and at least portion of the receptor are administered in a combination, the at least portion of the receptor binds to the cytokine and thus alters the binding properties of the cytokine to receptors in vivo. Thus, in a presently preferred embodiment, the peptide binds to the cytokine.

The pharmaceutical composition may be in any form suitable for administration. In a preferred embodiment, the pharmaceutical composition is in a form suitable for injection. The peptide of the pharmaceutical composition may comprise a sequence selected from SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11 and SEQ ID No. 12, described below. The peptide of the pharmaceutical composition may have at least 70% homology with any one of 30 the peptides SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11 and SEQ ID No. 12, and be capable of binding to the chemokine.

One or more amino acids in the peptide may be a steric enantiomer (D isomer), a rare amino acid of plant origin, an unnatural amino acid or amino acid mimetic, or a chemically modified amino acid. Such chemically modified amino acids are well-known in the art and include amino acids modified by acetylation, acylation, phosporylation, dephosphorylation, glycosylation, myristollation, amidation, aspartic acid/asparagine hydroxylation, phosphopantethane attachment, methylation, methylthiolation, prensyl group attachment, intein N/C-terminal splicing, ADP-ribosylation, bromination, citrullination, deamination, dihydroxylation, formylation, geranyl-geranilation, glycation, or palmitoylation.

In its second aspect, the invention provides use of the pharmaceutical composition of the invention for altering immune system functioning, such as an autoimmune disease, multiple sclerosis, transplant rejection, psoriasis and asthma.

In its third aspect, the invention provides a method for treating an immune system disorder comprising administering to an individual in need of such treatment a pharmaceutical composition comprising:
(a) A cytokine;
(b) A peptide comprising at least a portion of a cytokine receptor or a GPCR; and
(c) A physiologically acceptable carrier.

In its fourth aspect, the invention provides a method for preparing a pharmaceutical composition, the pharmaceutical composition comprising:
(a) a solubilized cytokine; and
(b) a solubilized peptide comprising at least a portion of a cytokine receptor or a GPCR; the method comprising combining the cytokine and the peptide ex vivo.

In its fifth aspect, the invention provides a peptide selected from:
(c) SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11 and SEQ ID No. 12;
(d) a peptide having at least 70% homology with a peptide of (a) capable of binding to a cytokine; and
(e) a peptide of (a) or (b) wherein at least one amino acid has been chemically modified.

BRIEF DESCRIPTION OF THE DRAWINGS

In order to understand the invention and to see how it may be carried out in practice, embodiments will now be described, by way of non-limiting example only, with reference to the accompanying drawings, in which.

EXAMPLES

Figure 1:
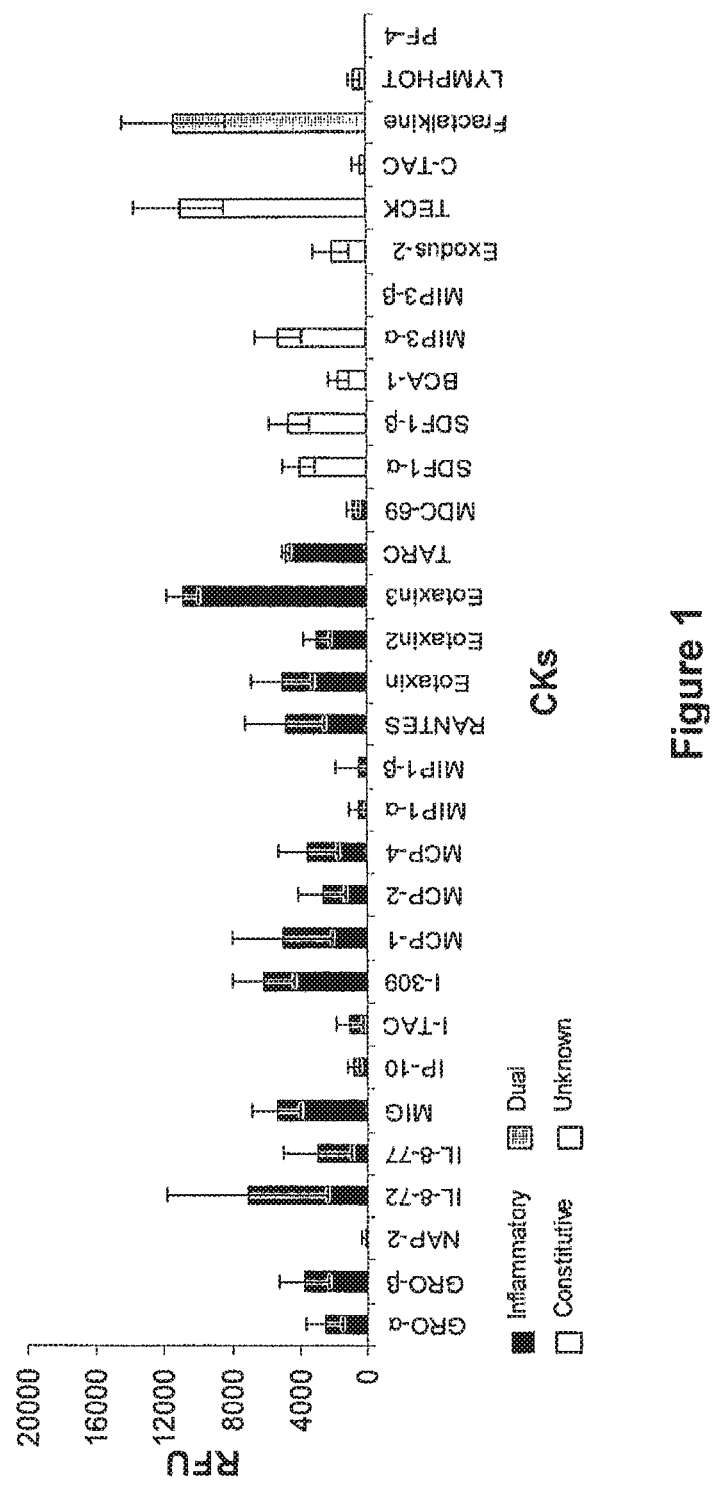
FIG. 1 shows chemokine binding of Chemokine Binding Peptide (CBP) 5.

Materials and Methods
Chemokines (CKs):
the following CKs were obtained from PreproTech Inc. (Rocky Hill, N.J. USA)
Inflammatory CKs:
(1) GRO-α (CXCL1 cat. no. 300-11), (2) GRO-β (CXCL2 cat. no. 300-39), (3) NAP-2 (CXCL7 cat. no. 300-14), (4) IL-8(72aa) (CXCL8 cat. no. 200-08M), (5) IL-8(77aa) (CXCL8 cat. no. 200-08), (6) MIG (CXCL9 cat. no. 300-26), (7) IP-10 (CXCL10 cat. no. 300-12), (8) I-TAC (CXCL11 cat. no. 300-46), (9) 1-309 (CCL1 cat. no. 300-37), (10) MCP-1 (CCL2 cat. no. 300-04), (11) MCP-2 (CCL8 cat. no. 300-15), (11) MCP-4 (CCL13 cat. no. 300-24), (12) MIP-la (CCL3 cat. no. 300-08), (13) MIP-la (CCL4 cat. no. 300-09), (14) RANTES (CCL5 cat. no. 300-06), (15) Eotaxin (CCL11 cat. no. 300-21), (16) Eotaxin 2 (CCL24 cat. no. 300-33), (17) Eotaxin 3(CCL26 cat. no. 300-48).

Constitutive CKs:
(1) TARC (CCL17 cat. no. 300-30), (2) MDC(69aa), (CCL22 cat. no. 300-36A), (3) SDF-1α(CXCL12 cat. no. 300-28a), (4) SDF-113 (CXCL12 cat. no. 300-28b), (5) BCA-1 (CXCL13, cat. no. 300-47), (6) MIP-3α (CCL20 cat. no. 300-29A), (7) MIP-3β (CCL19 cat. no. 300-29B), (8) Exodus-2 (CCL21 cat. no. 300-35), (9) TECK (CCL25 cat. no. 300-45), (10) CTAC (CCL2? cat. no. 300-54).

Dual Function (Inflammatory and Constitutive) CKs:
(1) Fractalkine (CX3CL1 cat. no. 300-31), (2) Lymphotactin (XCL-1 cat. no. 300-20), (3) PF-4 (CXCL4 cat. no. 300-16).

The following 13 amino acid sequences were from CKR regulatory regions were used SEQ ID No. 1: SYYDDVGL, referred to herein as "Peptide 1". Origin: N-terminus of human C—C chemokine receptor type 3 (CCR3; Eosinophil Eotaxin receptor). The biotinylated peptide (N-terminus) was synthesized by BiomerTechnology, USA and dissolved in DMSO (0.05% in H₂0).

SEQ ID No. 2: WVFGHGMCK, referred to herein as "Peptide 2". Origin: Extra Cellular Loop (ECL)-2 of human C—C chemokine receptor type 3 (CCR3; Eosinophil Eotaxin receptor). The biotinylated peptide (N-terminus) was synthesized by Sigma, Israel and dissolved in H₂O.

SEQ ID No. 3: LFGNDCE, referred to herein as "Peptide 5". Origin: ECL-4 of human C—C chemokine receptor type 3 (CCR3; Eosinophil Eotaxin receptor). The biotinylated peptide (N-terminus) was synthesized by Sigma, Israel and dissolved in H₂0.

SEQ ID No. 4: WVFGTFLCK, referred to herein as "Peptide 7". Origin: ECL-2 of human C—C chemokine receptor type 2 (CCR2; Monocyte Chemoattractant Protein 1 receptor). The biotinylated peptide (N-terminus) was synthesized by BiomerTechnology, USA and dissolved in DMSO (0.1% in H₂0).

SEQ ID No. 5: WVFGNAMCK, referred to herein as "Peptide 8". Origin: ECL-2 of human C—C chemokine receptor type 2 (CCR2; Monocyte Chemoattractant Protein 1 receptor). The biotinylated peptide (N-terminus) was synthesized by BiomerTechnology, USA and dissolved in DMSO (0.1% in H$_2$0).

SEQ ID No. 6: FFGLNNC, referred to herein as "Peptide 10". Origin: ECL-4 of human C—C chemokine receptor type 5 (CCR5; HIV-1 Fusion Co-receptor). The biotinylated peptide (N-terminus) was synthesized by BiomerTechnology, USA and dissolved in DMSO (0.1% in H$_2$0).

SEQ ID No. 7: TTFFDYDYG, referred to herein as "Phage-presented (Ph) Peptide 11". Origin: N-terminus of human C—C chemokine receptor type 2 (CCR2; Monocyte Chemoattractant Protein 1 receptor). The recombinant peptide was cloned in and expressed by the M13 cloning vector.

SEQ ID No. 8: EDSVY, referred to herein as "Ph-Peptide 13". Origin: ECL-3 of human C—C chemokine receptor type 2 (CCR2; Monocyte Chemoattractant Protein 1 receptor). The recombinant peptide was cloned in and expressed by the M13 cloning vector.

SEQ ID No. 9: WVFGSGLCK, referred to herein as "Ph-Peptide 15". Origin: ECL-2 of human C—X—C chemokine receptor type 2 (CXCR3; Interferon-inducible protein 10 receptor). The recombinant peptide was cloned in and expressed by the M13 cloning vector.

SEQ ID No. 10: HHTCSLHFP, referred to herein as "Ph-Peptide 16". Origin: ECL-3 of human C—C chemokine receptor type 1 (CCR1; Macrophage inflammatory protein 1-alpha receptor). The recombinant peptide was cloned in and expressed by the M13 cloning vector.

SEQ ID No. 11: HYTCSSHFP, referred to herein as "Ph-Peptide 17". Origin: ECL-3 of human C—C chemokine receptor type 5 (CCR5; HIV-1 Fusion Co-receptor). The recombinant peptide was cloned in and expressed by the M13 cloning vector.

SEQ ID No. 12: DRYLNIVHAT, referred to herein as "Ph-Peptide 18". Origin: ECL-3 of human C—X—C chemokine receptor type 3 (CXCR3; Interferon-inducible protein 10 receptor). The recombinant peptide was cloned in and expressed by the M13 cloning vector.

SEQ ID No. 13: TKCQKE, referred to herein as "Ph-Peptide 20". Origin: ECL-3 of human C—C chemokine receptor type 2-(CCR2; Monocyte Chemoattractant Protein 1 receptor). The recombinant peptide was cloned in and expressed by the M13 cloning vector.

Micro-Array Analysis of Chemokine Binding Peptides
  (1) Printing: Chemokine (CK) solution (in water) was serially diluted with Print Reagent (GenTel BioSurfaces USA) to final concentrations of 50 and 25 g/ml. BSA (Amresco, Cat. No. 0032-256)/BSA-Biotin (Sigma, Cat. No. A8549) control solutions (in water) were diluted with Print Reagent to 100 µg/ml. An automated spotting robot (16 pin print tool, 0.4 mm head; BioRobotics, UK) was used to print the CK/BSA control, 5 repeats per sample (25 µg/ml and 50 µg/ml), on PATH Protein Microarray Slides (GenTel, Prod. No. 2-1005/-1025) at 20°-30° C., and 50-70% relative humidity. Printed micro-array slides were stored at Room. Temperature or 4° C. for at least 24h before use.
  (2) Blocking: Block Buffer (500 µl/partition; PATHblock, GenTel, Prod. No. 2-1014) was applied to the slide for 1 hour at room temp (RT). After removal of Block Buffer, the slide was air dried for 25 minutes;
  (3) Peptide Binding: The peptide was applied in Wash Buffer, 300 µl (GenTel, PATHwash, Prod. No. 2-1016), per partition and incubated at RT for 1 hour with gentle agitation;
  (4) Washing: The slides were washed twice with Wash Buffer (300 µl/partition);
  (5) First Label Binding: The slides were incubated while protected from direct light with Cy3-labeled streptavidin (1 mg/ml, 300 µl/partition; DyLight 547, Pierce Prod. No. 21424) for 45 minutes at RT;
  (6) First Washing: The slides were washed twice with Wash Buffer (300 µl/partition);
  (7) Second Label Binding: Step (5) was repeated;
  (8) Second Washing: Step (6) was repeated;
  (9) Rinse: the slides were rinsed twice with Rinse Buffer (PATHrinse, GenTel, Prod. No. 2-1018) then dried well;
  (10) Scanning: The peptide-bound, labeled slide was scanned (Laser Intensity 60%, Gain 80%, Resolution 10 µm) with a ScanArray Life Scanner (Packard BioChip Technologies, USA);
  Analysis:
  Quantitative analysis of micro-array was performed by the SpotReader program of Niles Scientific (USA) and presented as Relative Fluorescence (RF) as a function of CK concentration. Micro-array readout (Cy3 fluorescence) was quantified to determine the relative binding affinities of a CBP for the CKs and by inference, the specificity of the CBP for binding to a CK.

Micro-Array Analysis of Phage Presented Chemokine Binding Peptides
  (1) Printing: Chemokine (CK) solution (in water) was serially diluted with Print Reagent (GenTel BioSurfaces USA) to final concentrations of 50 µg and 25 µg/ml. BSA/BSA-Biotin control solutions (in water) were diluted with Print Reagent to 100 µg/ml. Amplified stock of M13 phage control (M13KEgIII Cloning Vector, New England Biolabs, Cat. No. E8101S) was stored in Tris Buffered Saline (TBS; pH7.5, 4° C.) and diluted with Print Reagent to the working titre (10$^8$ pfu/µl). An automated spotting robot (16 pin print tool, 0.4 mm head; BioRobotics, UK) was used to print the CK/BSA control/M13 control, 5 repeats per sample (CK 25 µg/ml and 50 µg/ml; BSA 100 µg/ml; M13 20 µl), on PATH Protein Microarray Slides (GenTel, Prod. No. 2-1005/-1025) at 20°–30° C., and 50-70% relative humidity. Printed micro-array slides were stored at Room. Temperature or 4° C. for at least 24h before use.
  (2) Blocking: Block Buffer (500 µl/partition; PATHblock, GenTel, Prod. No. 2-1014) was applied to the slide for 1 hour at room temp (RT). After removal of Block Buffer, the slide was air dried for 25 minutes;
  (3) Phage Presented Peptide Binding: Amplified recombinant phage stock was stored in TBS and diluted with Wash Buffer to working titer (10$^7$ pfu/µl). Recombinant phage suspension (300 µl) was applied per partition and incubated at RT for 1 hour with gentle agitation.
  (4) First Washing: The slides were washed twice with Wash Buffer (300u/partition);
  (5) Primary Antibody (Ab) Labeling: The slides were incubated with the Primary Ab (1 mg/ml diluted×2500 (Wash Reagent), 300 µl; Mouse Anti-M13 monoclonal Ab; Amersham Biosciences, UK; Product Code 27-9420-01) for 45 minutes at RT;
  (6) Second Washing: The slides were washed twice with Wash Buffer (300 µl/partition);
  (7) Secondary Ab Labeling: The slides were incubated with Secondary Ab (1.5 mg/ml diluted×5000 (Wash Reagent), 300 µl; Cy3-conjugated AffiniPure Goat Anti-Mouse IgG; Jackson ImmunoReserch Labs, USA; Product Code 115-165-062).

(8) Third Washing: The slides were washed twice with Wash Buffer (300 µl/partition);

(9) Rinse: The slides were rinsed twice with Rinse Buffer (PATHrinse, GenTel, Prod. No. 2-1018) then dried well;

(10) Scanning: The peptide-bound, labeled slide was scanned (Laser Intensity 80%, Gain 80%, Resolution 10 µm) with a ScanArray Life Scanner (Packard BioChip Technologies, USA);

(11) Analysis: Quantitative analysis of micro-array was performed by the SpotReader program of Niles Scientific (USA) and presented as Relative Fluorescence (RF) as a function of CK concentration. Micro-array readout (Cy3 fluorescence) was quantified to determine the relative binding affinities of a CBP for the CKs and by inference, the specificity of the CBP for binding to a CK.

CK-Peptide Combination

Test samples which comprised specific combinations of CKs and Peptides were prepared by mixing the CK and Peptide in a tube and storing the mixture on ice for 1 hour to 3 hours before injection into an experimental animal.

Anti-Inflammatory Control Reagent

Dexamethasone Sodium Phosphate (Dexacort Forte, Teva) was dissolved in Phosphate Bufer Saline (PBS, GIBCO) to a final concentration of 1 mg/ml and injected in 200 µl (200 µg).

The Animal Model of Disease (General Inflammation): Delayed Type Hypersensitivity Delayed-type hypersensitivity (DTH) reactions are antigen-specific, cell-mediated immune responses that, depending on the antigen, mediate beneficial (e.g. resistance to viruses, bacteria and fungi), or harmful (e.g. allergic dermatitis and autoimmunity) aspects of immune function. They are commonly used as models of chronic inflammatory diseases, since they are both initiated by an antigen and perpetuated by antigen-specific T cells.

Peptides were tested in a mouse model for their anti- or pro-inflammatory effects.

Contact hypersensitivity (CHS) reaction in mice differs from typical skin-irritation models, in that, an agent such as oxazolone (4-ethoxymethylene-2-oxazolin-5-one) is used which is not a strong irritant and requires a sensitization exposure before challenge. The role of oxazolone-specific T cells has been demonstrated by the ability of purified T cells from sensitized donor mice to transfer reactivity into naive recipients [Asherson, 1968] and both CD4+ and CD8+ T cells are required to initiate the inflammatory response and recruit additional leukocytes [Gocinski, 1990].

Sensitization:

Animals (BalbC, female, age 7-8 weeks, 5 per group) were sensitized by application of oxazolone (Sigma E0753, 100 µl (2% (wt/vol) in oil (Kodak)) on abdominal skin, day 0.

Challenge:

The animals were challenged by application of oxazolone (10 µl (0.5% (wt/vol) in oil) to the left ear. 10 µl of the carrier (oil) was applied to the right ear, on day 6.

Treatment:

The test reagents (CK, Peptide, CK-Peptide combinations, Anti-Inflammatory Control) were prepared from frozen stocks (−20° C.) on the day of the treatment and stored on ice until injected intra-peritoneally (0.2 ml per injection), one hour before Challenge and one hour after Challenge.

Measurement:

Ear thickness was measured with a dial thickness gauge (Mitutoyo, Japan) twenty four hours after challenge, on day 7. The pro- and anti-inflammatory activities of individual peptides and CKs and complexes of peptides with CKs, were calculated relative to the anti-inflammatory activity of Dexamethasone (Dexa). Dexa is an anti-inflammatory standard which, in this example, reduced measured inflammation by 36% and served as a standard of 100% for calculated values of the pro- and anti-inflammatory activities of the test reagents. An anti-inflammatory effect was measured as a reduction in inflammation compared with the untreated group of animals and its value calculated relative to the efficacy of Dexa (100% anti-inflammatory effect). A pro-inflamatory effect was measured as an increase in inflammation compared with the untreated group and its value calculated relative to Dexa.

Results

Micro-array analysis of Chemokine Binding Peptide 5 (CBP5) to inflammatory, constitutively expressed and dual function CKs. FIG. 1 shows the binding affinity of CBP5 to several chemokines. CBP5 bound with relatively high affinity (>3 000 Relative Fluorescence Units (RFU), responses in the upper 75% range of 0-12000 RFUs) to the inflammatory CKs, Eotaxin, Eotaxin 3, MCP-4 and RANTES, cognate CK ligands of the receptor from which CBP5 is derived. The same peptide bound with relatively high affinity to IL-8, MIG, 1309, MCP-1 and TARC, unrelated inflammatory CK ligands of the CKR, CCR3. CBP5 also bound the constitutively expressed CKs, SDF1-a/1 $\beta$, MIP3-a and TECK and the dual function CK, Fractalkine, none of which is a cognate ligand of the CKR, CCR3.

Figure 2:
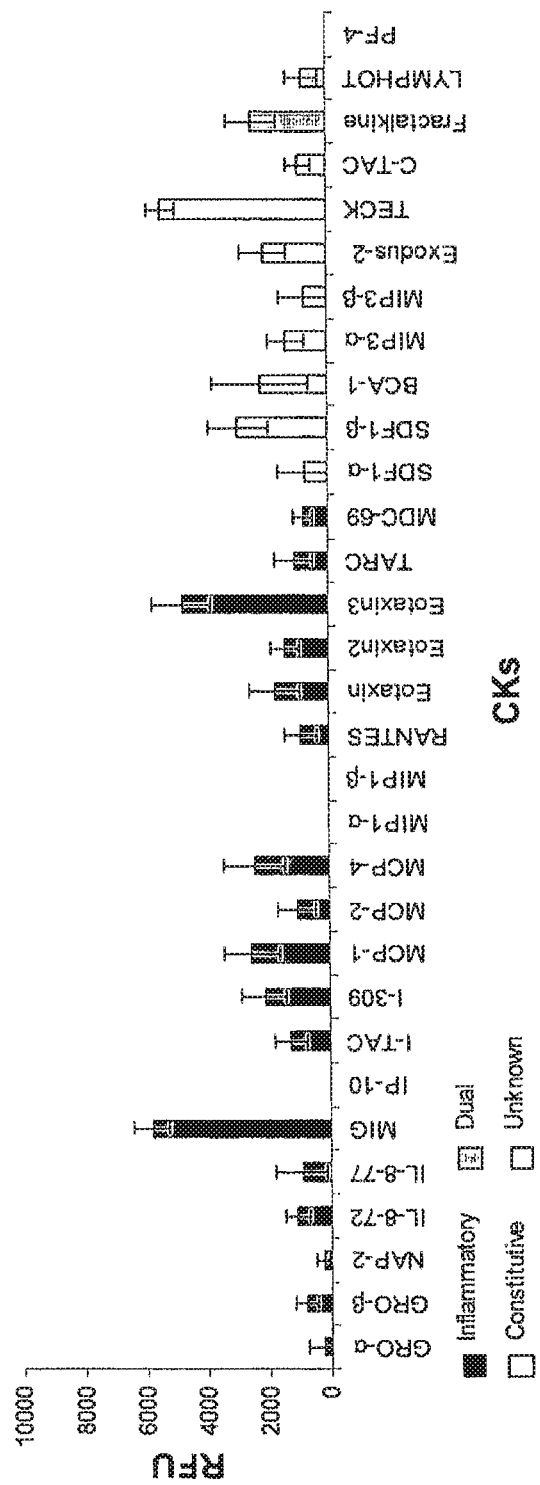
FIG. 2 shows chemokine binding of CBP 8.

Micro-array analysis of Chemokine Binding Peptide 8 (CBP8) binding to inflammatory, constitutively expressed and dual functions CKs. As shown in FIG. 2, CBP8 bound with relatively high affinity (>1500 Relative Fluorescence Units (RFU), responses in the upper 75% range of 0-6000 RFUs) to the inflammatory CKs, MCP-1 and -4, cognate CK ligands of the receptor from which CBP8 was derived. The same peptide bound with relatively high affinity to MIG, 1-309, Eotaxin, Eotaxin 3, and to the constitutively expressed CKs, SDF1-(3, BCA-1, Exodus-2, TECK, and the dual function CK, Fractalkine, all of which are unrelated CK ligands of the CKR from which CBP8 is derived.

Figure 3:
FIG. 3 shows chemokine binding of CBP 10.

Micro-array analysis of Chemokine Binding Peptide 10 (CBP10) binding to inflammatory, constitutively expressed and dual functions CKs. As shown in FIG. 3, CBP10 bound with relatively high affinity (>5000 Relative Fluorescence Units (RFU), responses in the upper 75% range of 0-20000 RFUs) to the inflammatory CK, MCP2, cognate ligand of the CKR from which CBP10 is derived. The same peptide bound with relatively high affinity to the inflammatory CKs, GRO-$\beta$, IP-10, I-TAC, 1-309, MCP-1, -4, Eotaxin, Eotaxin 2/3 and to the constitutively expressed CKs, SDF1-$\alpha$/1$\beta$ BCA-1 Exodus-2 and TECK, and the dual function CKs, Fractalkine and Lymphotactin, all of which are unrelated CK ligands of the CKR from which CBP10 is derived.

Figure 4A:
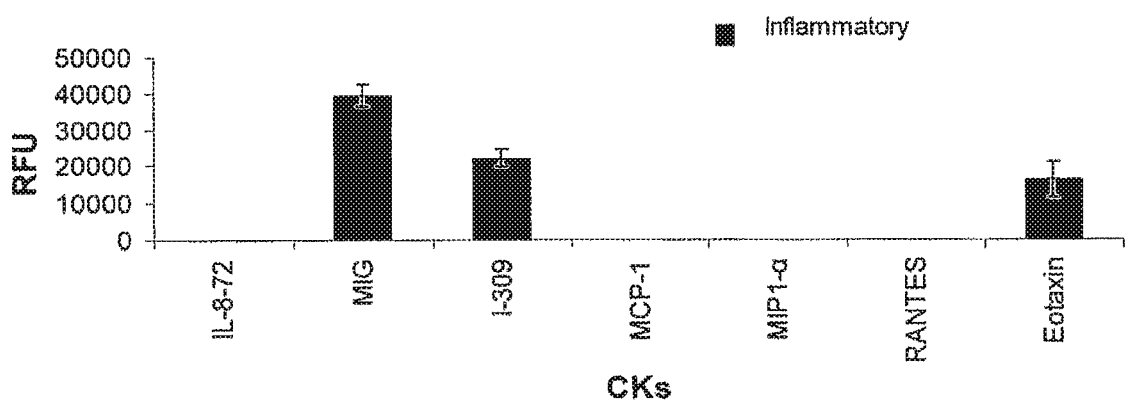
FIGS. 4A and 4B show chemokine binding CBP 2.
Figure 4B:
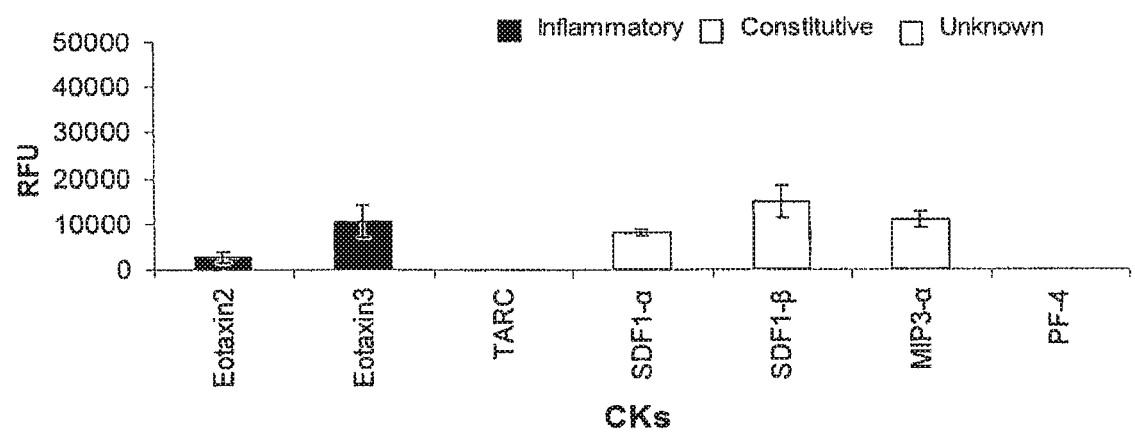

CBP2 (WVFGHGMCK (SEQ ID NO. 2); from the Extra Cellular Loop (ECL)-2 of human C—C CKR type 3 (CCR3)) CBP2 was screened against the human inflammatory CKs, IL-8(72aa; CXCL8), MIG (CXCL9), 1-309 (CCL1), MCP-1 (CCL2), MIP-1$\alpha$ (CCL3), RANTES (CCL5), (15) Eotaxin (CCL11), Eotaxin 2 (CCL24), Eotaxin 3 (CCL26), TARC (CCL17), the human constitutive CKs, SDF-1$\alpha$(CXCL12), SDF-1$\beta$ (CXCL12), MIP-3$\alpha$ (CCL20) and the CK, PF-4 (CXCL4). The results are shown in FIGS. 4A/B. Experimental readout (Cy3 fluorescence) was quantified to determine the relative binding affinities of CBPs for the CKs and by inference, the binding specificity of CBPs for the CKs. CBP2. bound with relatively high affinity (>10000 Relative Fluorescence Units (RFU), responses in the upper 75% range of 0-60000 RFUs) to the inflammatory CKs, Eotaxin and Eotaxin 3, cognate CK ligands of the receptor from which CBP2 is derived. The same peptide bound with relatively high affinity to the inflammatory CKs, MIG and 1-309 and the constitutively expressed CKs, SDF1-α/β and MIP3-α, all of which are unelated CK ligands of the CKR from which CBP2 is derived.

CBP2, derived from ECL-2 of the CKR, CCR3, bound with relatively high affinity to Eotaxin 3, cognate CK ligand of the receptor. CBP2 interaction with Eotaxin 3 is consistent with the physiological interaction of a CK with its cognate receptor. The same peptide bound with relatively high affinity to MIG and 1-309, unrelated inflammatory CK ligands of the CKR, CCR3. CBP2 also bound the constitutively expressed CKs, SDF1-α/β and MIP3-α, none of which is a cognate ligand of the CKR, CCR3. It is inferred from the latter observation that the unrelated inflammatory and constitutive CKs modify CCR2 activity by interacting with CBP2 sequence, in the structural context of the CKR, CCR3. Independent of its native CKR, CBP3 is a potential modulator of CK activity, that of cognate and unrelated CK ligands of the CKR, CCR3.

CBP7 (WVFGTFLCK (SEQ ID NO. 4); from ECL-2 of human C—C chemokine receptor type 2 (CCR2) Peptide 7 (CBP7) was screened against the human inflammatory CKs, IL-8(72aa; CXCL8), MIG (CXCL9), IP-10 (CXCL10), I-TAC (CXCL11), 1-309 (CCL1), MCP-1 (CCL2), MIP-1α (CCL3), RANTES (CCL5), Eotaxin (CCL11), Eotaxin 2 (CCL24), Eotaxin 3 (CCL26), TARC (CCL17), the human constitutive CKs, SDF-1α(CXCL12), (CXCL12), MIP-3α (CCL20) and the CK of undefined function, PF-4 (CXCL4) presented in micro-array format. The experimental readout (Cy3 fluorescence) was quantified to determine the relative binding affinities of the CBP for the CKs and by inference, the binding specificity of CBP7 for the CKs.

Figure 5:
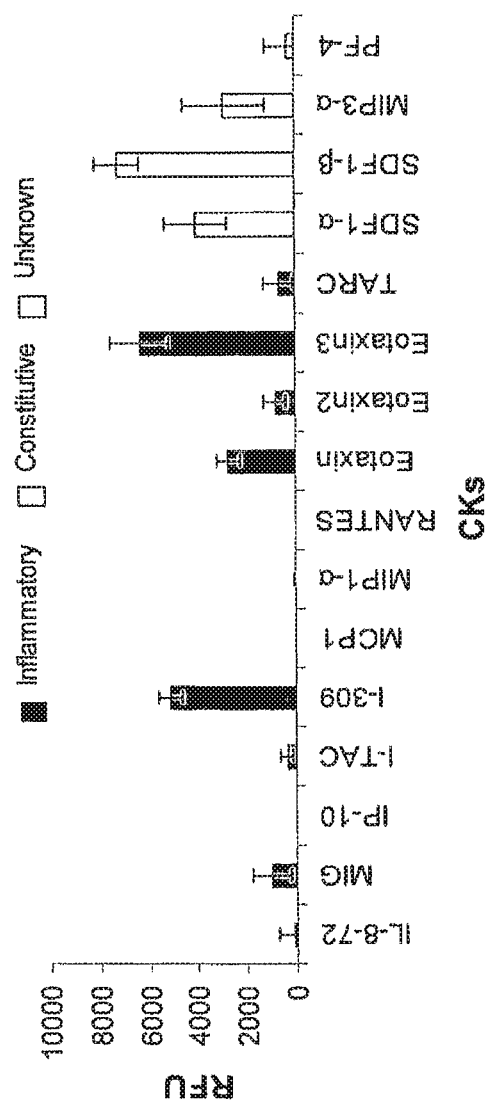
FIG. 5 shows chemokine binding of CBP 7.

The results are shown in FIG. 5. CBP7 bound with relatively high affinity (>2000 Relative Fluorescence Units (RFU), responses in the upper 75% range of 0-10000 RFUs) to the inflammatory CKs 1-309, Eotaxin and Eotaxin 3 and to the constitutively expressed CKs, SDF1-α. and -β, none of which is a cognate CK ligand of the CKR from which CBP7 is derived.

Figure 6:
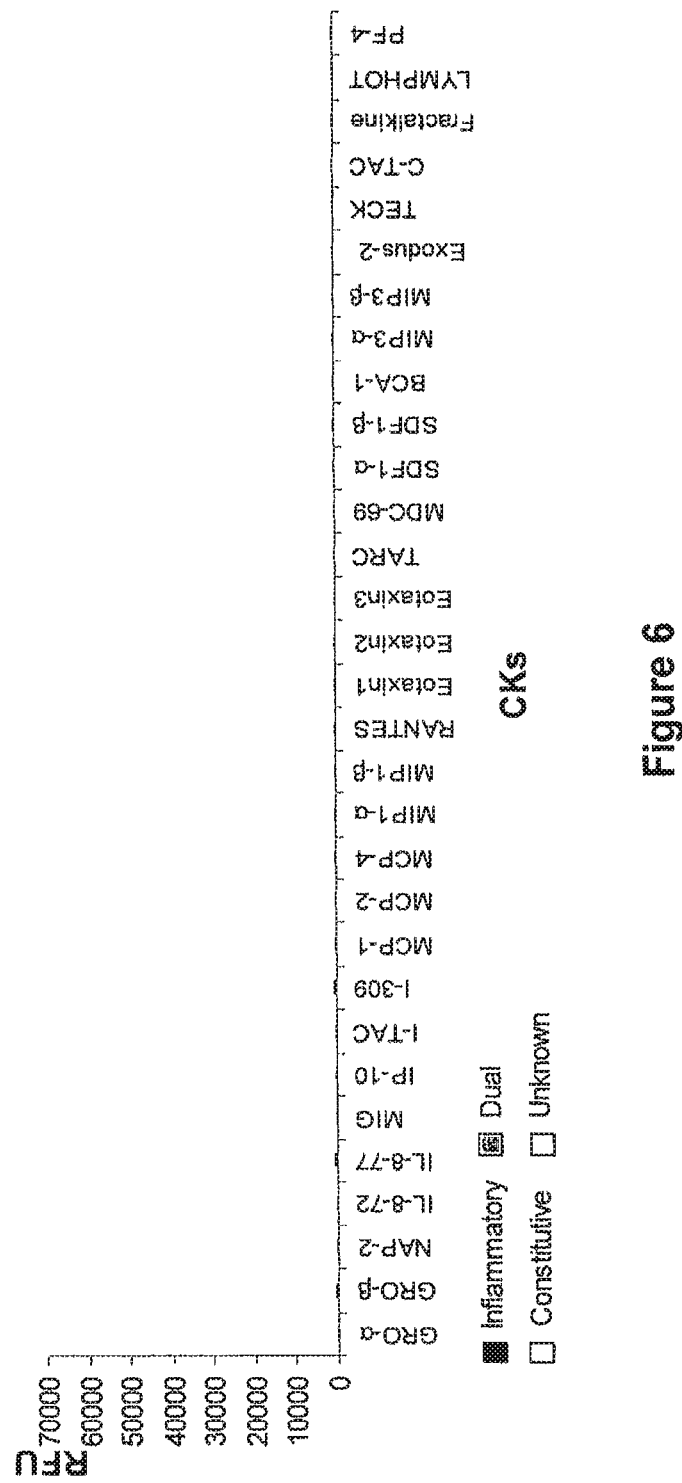
FIG. 6 shows a negative control micro-array analyses in the absence of CBP5, CBP8, and CBP10 peptides (negative controls) that were performed in parallel with the binding experiment of FIGS. 1, 2 and 3, respectively.
Figure 7:
FIG. 7 shows a negative control micro-array analyses in the absence of CBP7, (negative control) that was performed in parallel with the binding experiment of FIG. 5.
Figure 8A:
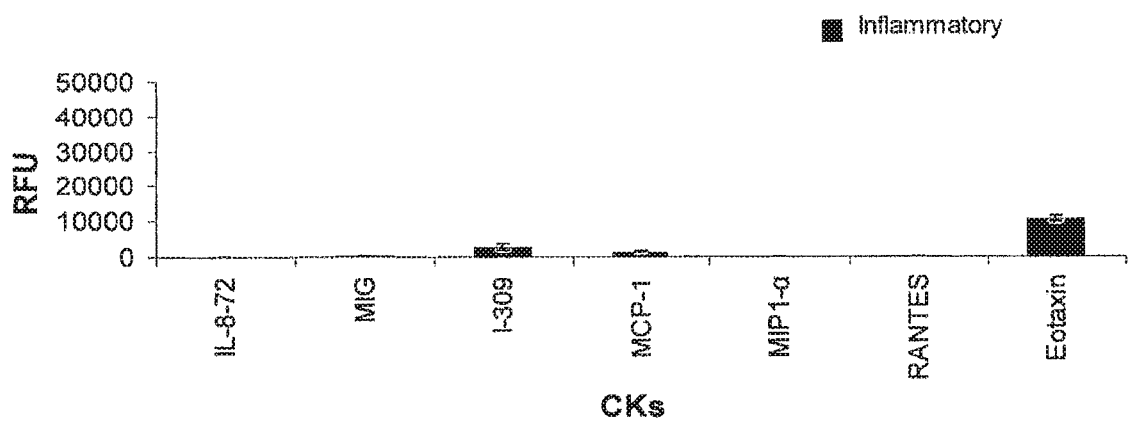
FIGS. 8A and 8B show a negative control micro-array analyses in the absence of CBP2, (negative control) that was performed in parallel with the binding experiment of FIG. 4.
Figure 8B:
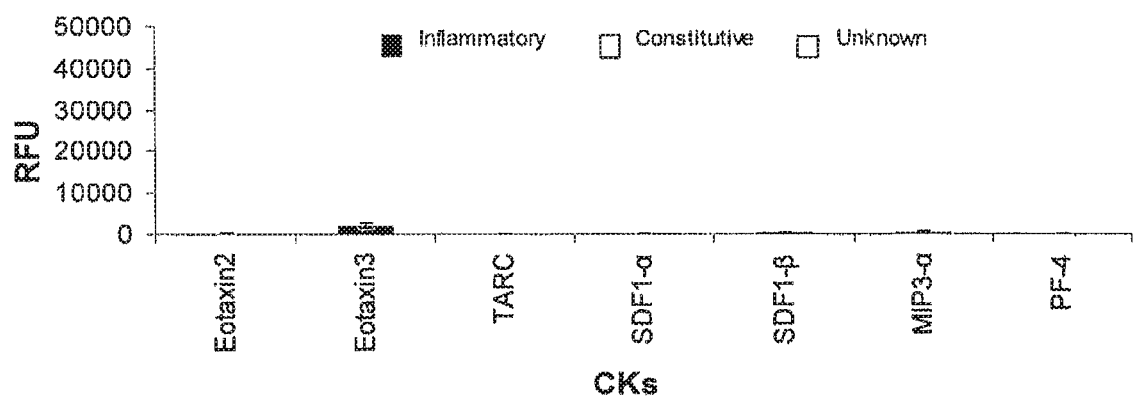

Negative Control Micro-array analyses for Chemokine Binding Peptides to inflammatory, constitutively expressed and dual function CKs. Micro-array analyses in the absence of peptide (negative controls) were performed in parallel with analyses in the presence of peptide. Negative control results for CBP5, -8, and 10 are shown in FIG. 6. Negative control results for CBP7 are shown in FIG. 7. Negative control results for CBP2 are shown in FIGS. 8A and 8B.

Figure 9:
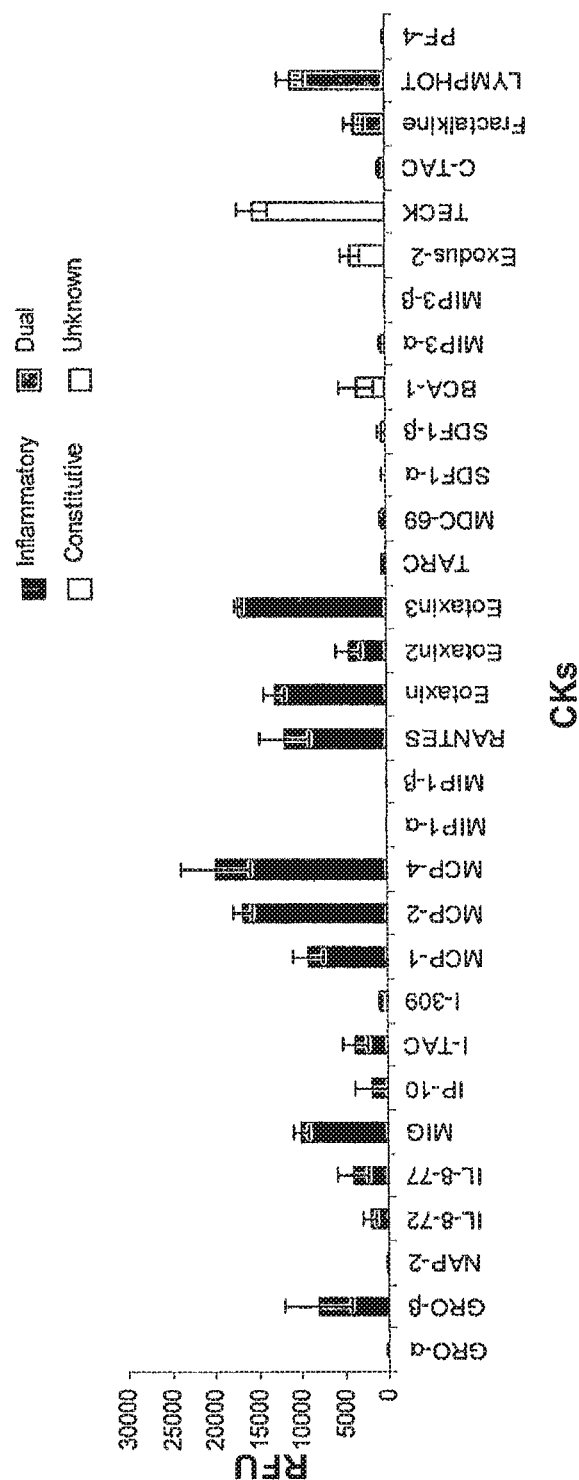
FIG. 9 shows chemokine binding of Phage-Presented Peptide (Ph-p) 11.

Micro-array analysis of Phage-Presented Peptide, Ph-pH, binding to 30 inflammatory, constitutively expressed and dual functions CKs. As shown in FIG. 9, Ph-p11 bound with relatively high affinity (>5000 Relative Fluorescence Units (RFU), responses in the upper 75% range of 0-20000 RFUs), to the inflammatory CKs, MCP-1, -2 and -4, cognate CK ligands of the receptor from which the peptide of Ph-p11 was derived. The same peptide bound with relatively high affinity to the inflammatory CKs, GRO-β, MIG, RANTES, Eotaxin, Eotaxin 3 and to the constitutively expressed CK, TECK, and the dual function Lymphotactin, all of which are unrelated CK ligands of the CKR from which the peptide of Ph-p 11 is derived. The RFU values of the recombinant phage were calculated by deducting the RFU value of the phage by itself (negative control).

Figure 10:
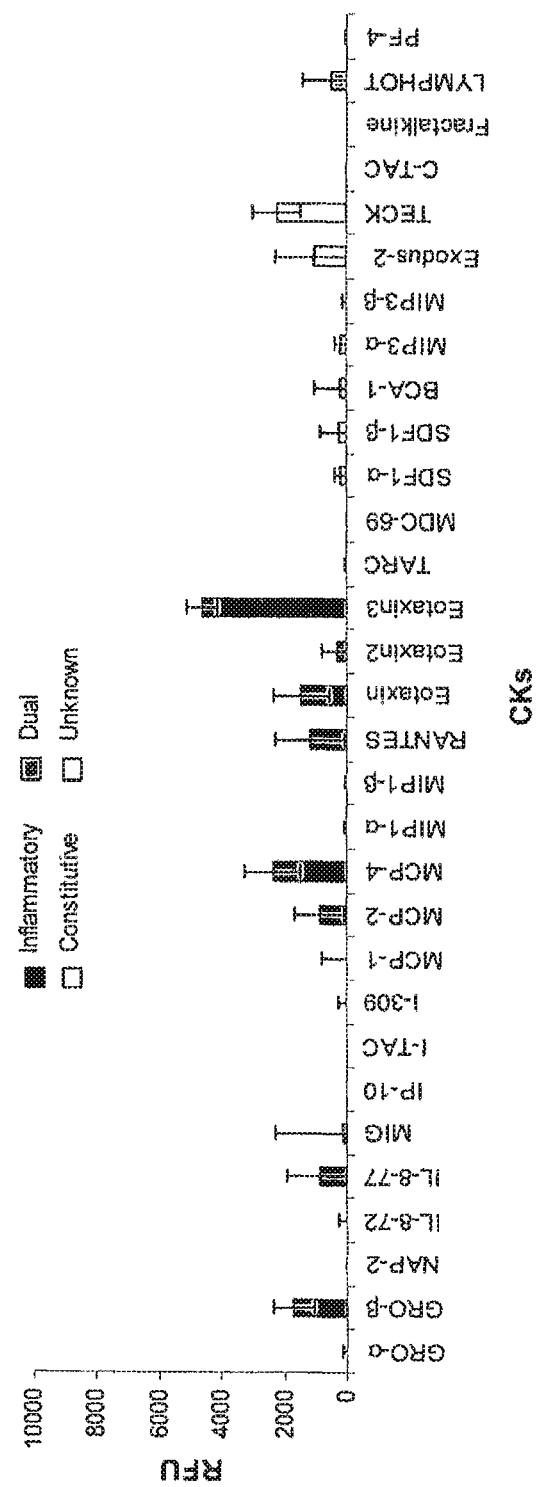
FIG. 10 shows chemokine binding of Ph-p13.

Micro-array analysis of Phage-Presented Peptide, Ph-p13, binding to inflammatory, constitutively expressed and dual functions CKs. As shown in FIG. 10, Ph-p13 bound with relatively high affinity (>1500 Relative Fluorescence Units (RFU), responses in the upper 75% range of 0-6000 RFUs) to the inflammatory CK, MCP-4, cognate CK ligand of the receptor from which the peptide of Ph-p13 was derived. The same peptide bound with relatively high affinity to the inflammatory CKs, GRO-β, Eotaxin, Eotaxin 3 and to the constitutively expressed CK, TECK, all of which are unrelated CK ligands of the CKR from which the peptide of Ph-p 13 is derived. The RFU values of the recombinant phage were calculated by deducting the RFU value of the phage by itself (negative control).

Figure 11:
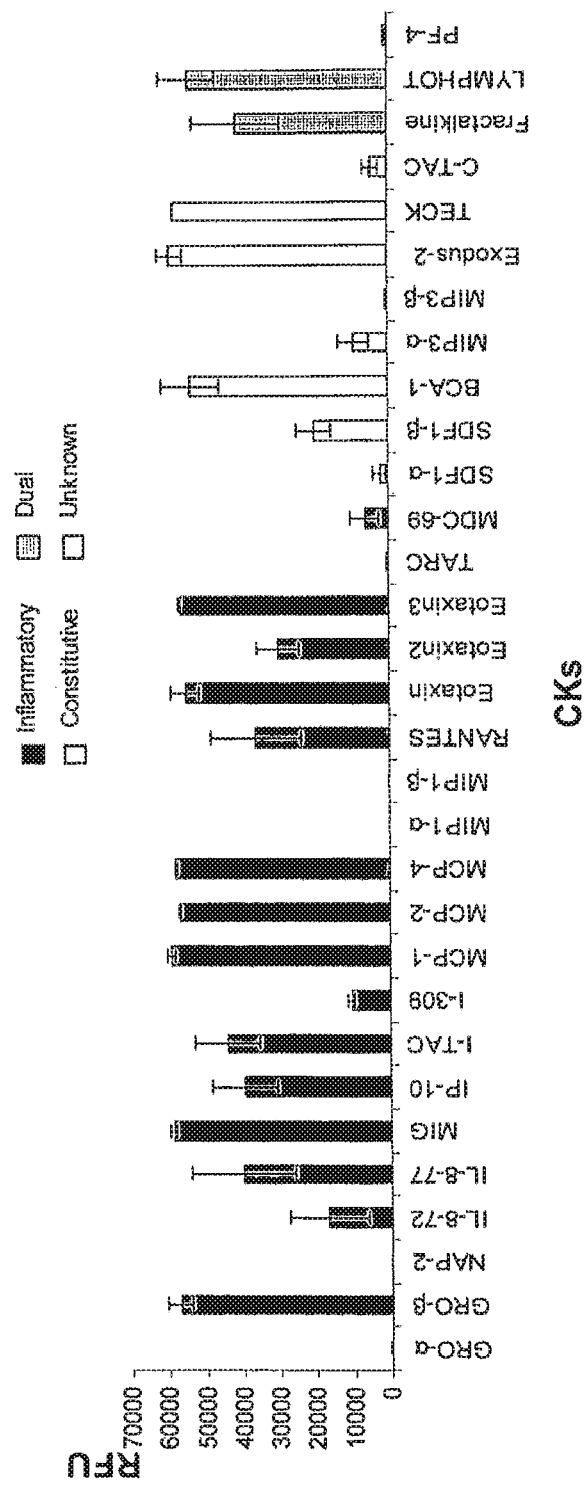
FIG. 11 shows chemokine binding of Ph-p15.

Micro-array analysis of Phage-Presented Peptide, Ph-p15, binding to inflammatory, constitutively expressed and dual functions CKs. As shown in FIG. 11, Ph-p15 bound with relatively high affinity (>30000 Relative Fluorescence Units (RFU), responses in the upper 50% range of 0-60000 RFUs) to the inflammatory CKs, MIG, IP-10 and I-TAC, cognate CK ligands of the receptor from which the peptide of Ph-p 15 was derived. The same peptide bound with relatively high affinity to the inflammatory CKs, GRO-13, IL-8 (77), MCP1/2/4, RANTES, Eotaxin, Eotaxin 2, Eotaxin 3 and to the constitutively expressed CKs, BCA-1, Exodus 2 and TECK and the dual function CKs, Fractalkine and Lymphotactin, all of which are unrelated CK ligands of the CKR from which the peptide of Ph-p 15 is derived. The RFU values of the recombinant phage were calculated by deducting the RFU value of the phage by itself (negative control).

Figure 12:
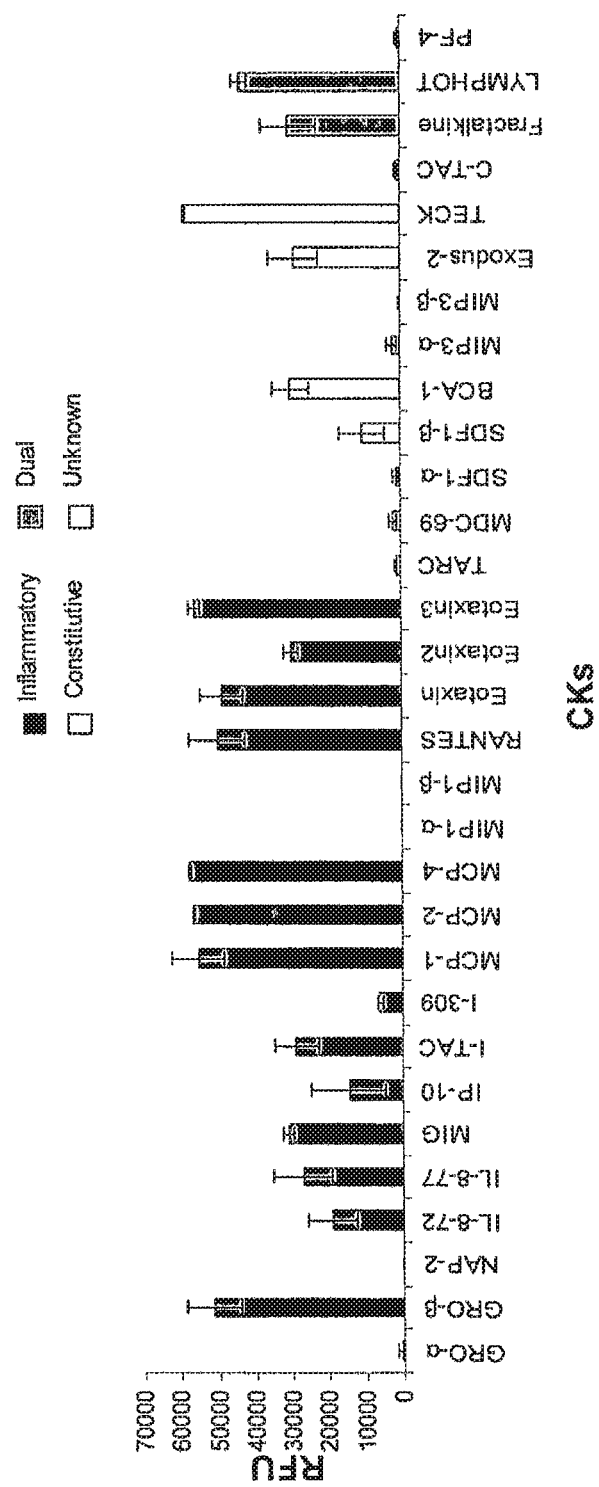
FIG. 12 shows chemokine binding of Ph-p16.

Micro-array analysis of Phage-Presented Peptide, Ph-p16, binding to inflammatory, constitutively expressed and dual functions CKs. As shown in FIG. 12, Ph-p16 bound with relatively high affinity (>30000 Relative Fluorescence Units (RFU), responses in the upper 50% range of 0-60000 RFUs) to the inflammatory CKs, MCP-4 and RANTES, cognate CK ligands of the receptor from which the peptide of Ph-p 16 was derived. The same peptide bound with relatively high affinity to the inflammatory CKs, GRO-β, MIG, MCP1/2, Eotaxin, Eotaxin 2, Eotaxin 3 and to the constitutively expressed CKs, BCA-1, Exodus 2 and TECK and the dual function CKs, Fractalkine and Lymphotactin, all of which are unrelated CK ligands of the CKR from which the peptide of Ph-p16 is derived. The RFU values of the recombinant phage were calculated by deducting the RFU value of the phage by itself (negative control).

Figure 13:
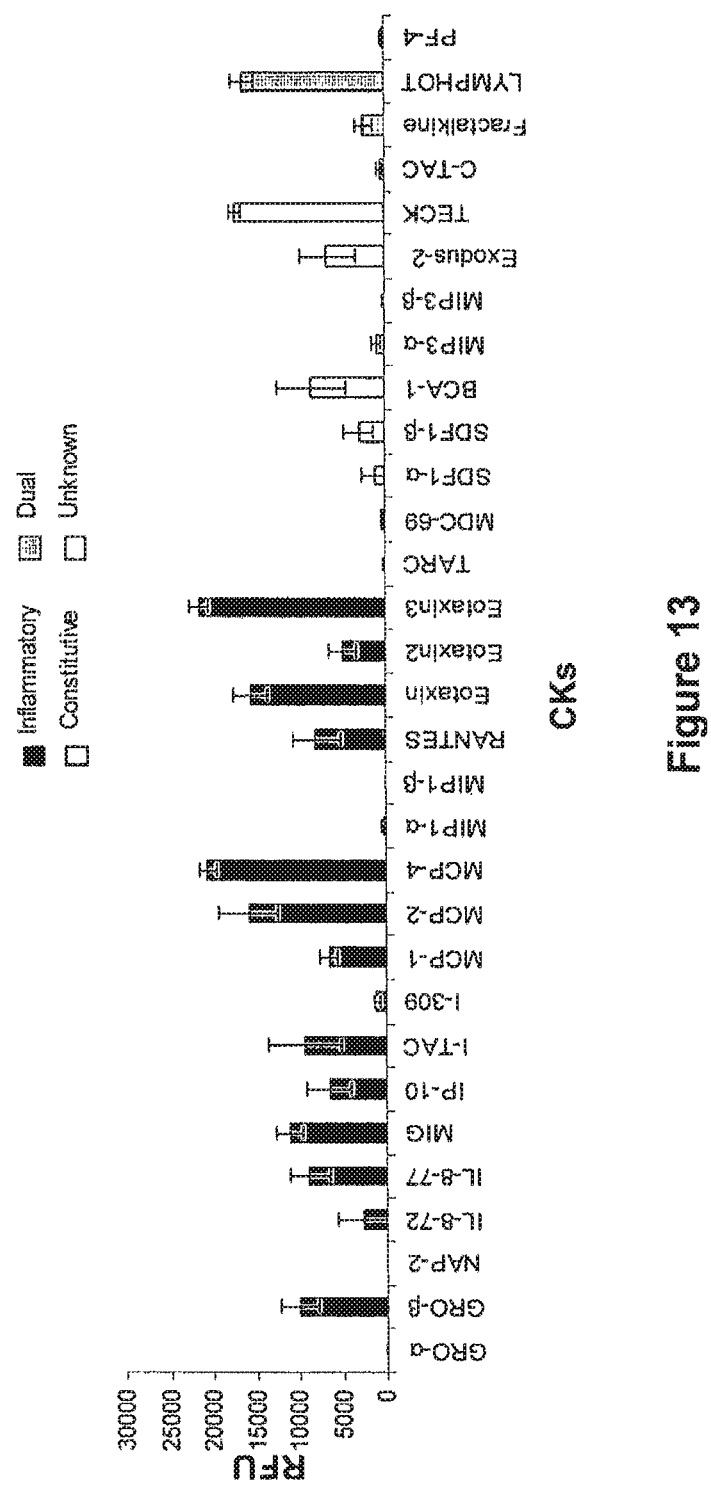
FIG. 13 shows chemokine binding of Ph-p17.

Micro-array analysis of Phage-Presented Peptide, Ph-p17, binding to inflammatory, constitutively expressed and dual functions CKs. As shown in FIG. 13, Ph-p17 bound with relatively high affinity (>4500 Relative Fluorescence Units (RFU), responses in the upper 75% range of 0-22000 RFUs) to the inflammatory CKs, MCP-2 and RANTES, cognate CK ligands of the receptor from which the peptide of Ph-p 17 was derived. The same peptide bound with relatively high affinity to the inflammatory CKs, GRO-β, IL-8 (77), MIG, IP-10, I-TAC, MCP1/4, Eotaxin, Eotaxin 2 and Eotaxin 3 and to the constitutively expressed CKs, BCA-1, Exodus 2 and TECK and the dual function CK Lymphotactin, all of which are unrelated CK ligands of the CKR from which the peptide of Ph-p17 is derived. The RFU values of the recombinant phage were calculated by deducting the RFU value of the phage by itself (negative control).

Figure 14:
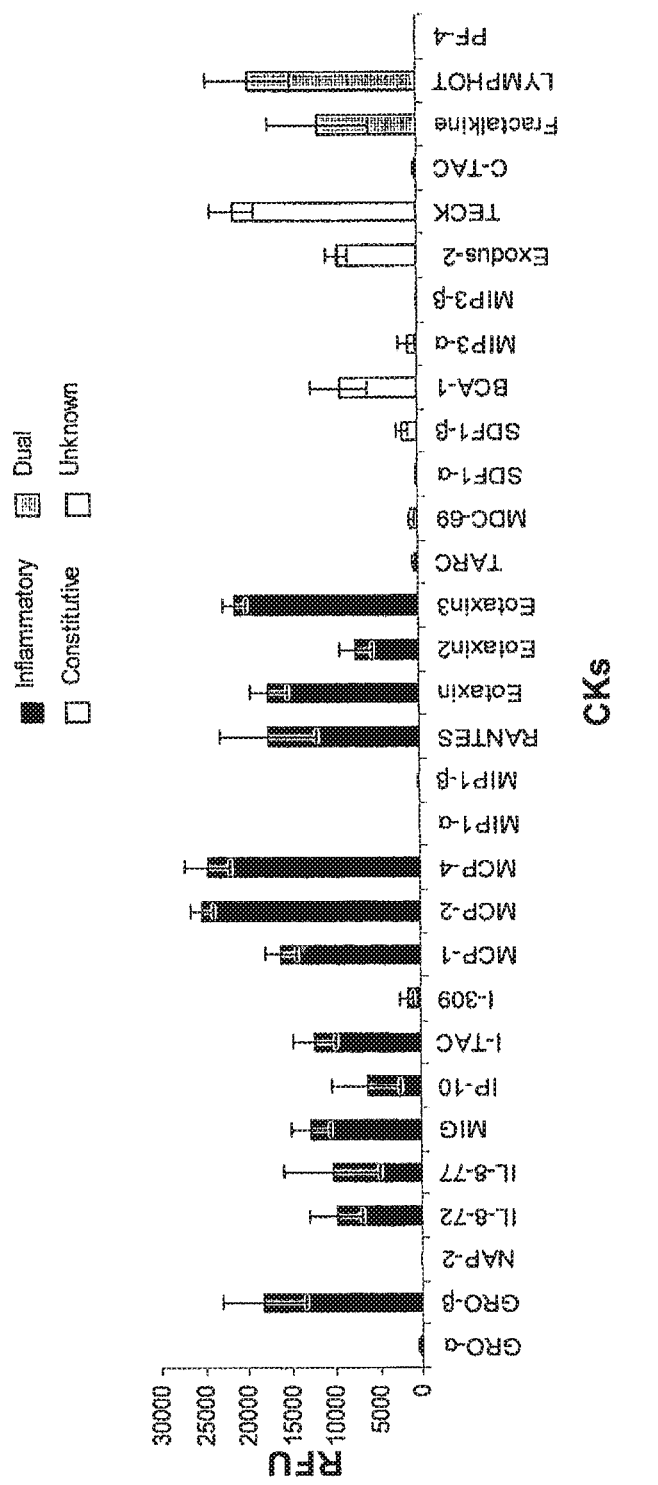
FIG. 14 shows chemokine binding of Ph-p18.

Micro-array analysis of Phage-Presented Peptide, Ph-p18, binding to inflammatory, constitutively expressed and dual functions CKs. As shown in FIG. 14, Ph-p18 bound with relatively high affinity (>6500 Relative Fluorescence Units (RFU), responses in the upper 75% range of 0-26000 RFUs) to the inflammatory CKs, MIG and 1-TAC cognate CK ligands of the receptor from which the peptide of Ph-p18 was derived. The same peptide bound with relatively high affinity to the inflammatory CKs, GRO-β, IL-8 (72), IL-8 (77), MCP1/2/4, RANTES, Eotaxin, Eotaxin 2, Eotaxin 3 and to the constitutively expressed CKs, BCA-1, Exodus 2 and TECK and the dual function CKs, Fractalkine and Lymphotactin, all of which are unrelated CK ligands of the CKR from which the peptide of Ph-p18 is derived. The RFU values of the recombinant phage were calculated by deducting the RFU value of the phage by itself (negative control).

Figure 15:
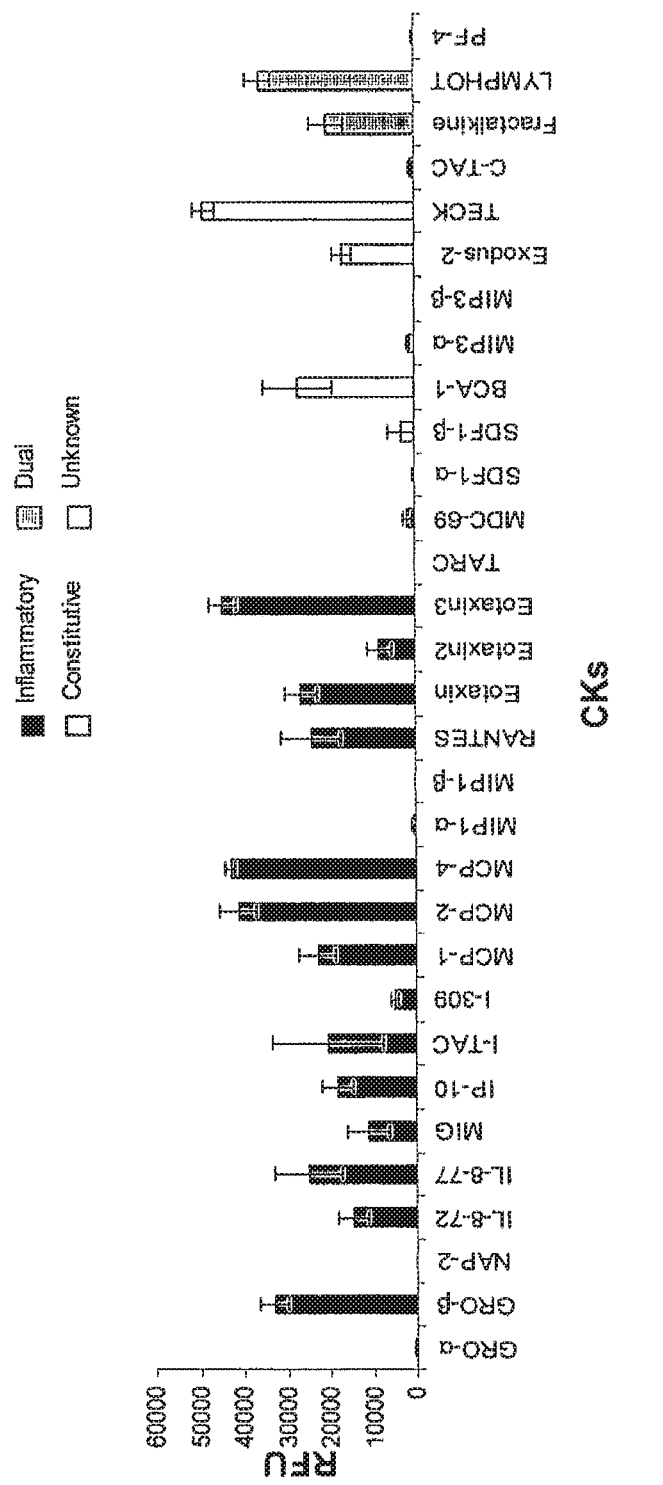
FIG. 15 shows chemokine binding of Ph-p20.

Micro-array analysis of Phage-Presented Peptide, Ph-p20, binding to inflammatory, constitutively expressed and dual functions CKs. As shown in FIG. 15, Ph-p20 bound with relatively high affinity (>12500 Relative Fluorescence Units (RFU), responses in the upper 75% range of 0-50000 RFUs) to the inflammatory CKs, MCP-1, -2 and -4, cognate CK ligands of the receptor from which the peptide of Ph-p20 was derived. The same peptide bound with relatively high affinity to the inflammatory CKs, GRO-β, IL-8 (72), IL-8 (77), IP-10, I-TAC, RANTES, Eotaxin, Eotaxin 3 and to the constitutively expressed CKs, BCA-1, Exodus 2 and TECK and the dual function CKs, Fractalkine and Lymphotactin, all of which are unrelated CK ligands of the CKR from which the peptide of Ph-p20 is derived. The RFU values of the recombinant phage were calculated by deducting the RFU value of the phage by itself (negative control).

Figure 16:
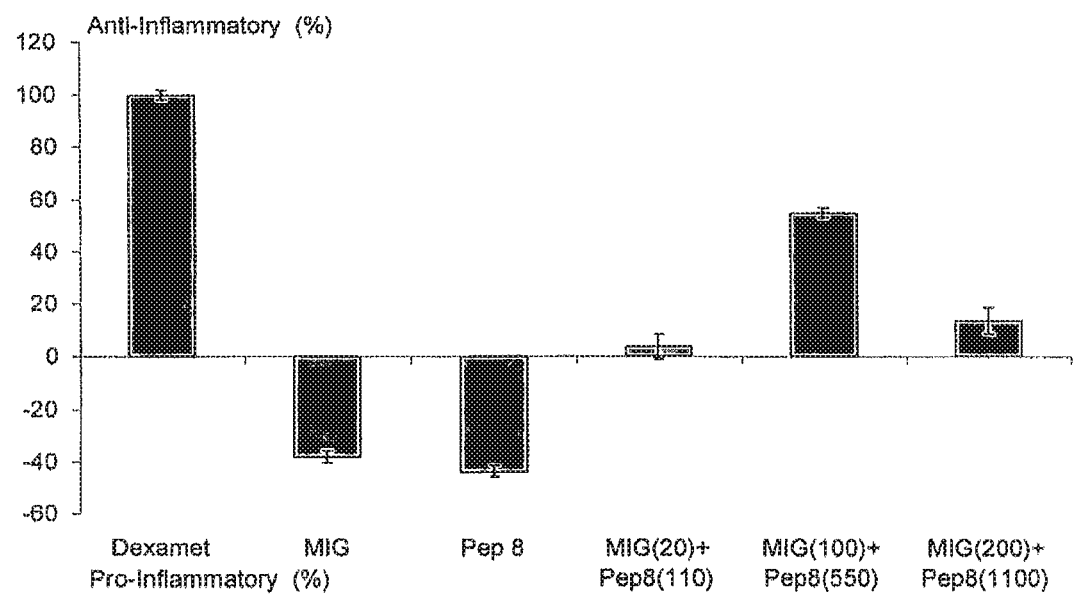
FIG. 16 shows the effect of CBP 8 combined with the CK, MIG when administered to disease, Delayed Type Hypersensitivity (DTH), -induced mice.

Efficacy of the CK MIG (CXCL9), Peptide 8 and different doses of Peptide 8 combined with MIG. The CK MIG, is expressed at elevated levels in inflammatory conditions and defined as an inflammatory CK. As shown in FIG. 16, 200 ng MIG, administered to disease induced mice was pro-inflammatory, increasing inflammation by 38% (−38 in FIG. 16) compared with disease-induced, untreated animals. 1100 ng Peptide 8 had a pro-inflammatory effect when administered to disease-induced mice, increasing inflammation by 44% (−44) compared with disease-induced, untreated animals. A combination of MIG and Peptide 8 had an anti-inflammatory effect when administered to the disease-induced animals. With a dose consisting of 20 ng MIG and 100 ng Peptide 8, the anti-inflammatory effect was 5% (5), compared with disease-induced, untreated animals. With a dose consisting of 100 ng MIG: and 550 ng Peptide 8, and with a dose consisting of 200 ng MIG and 1000 ng Peptide 8, the anti-inflammatory effect was 55% (55) and 14% (14), respectively. The molecular ratio of the respective doses was 1:50 (CK: Peptide).

Figure 17:
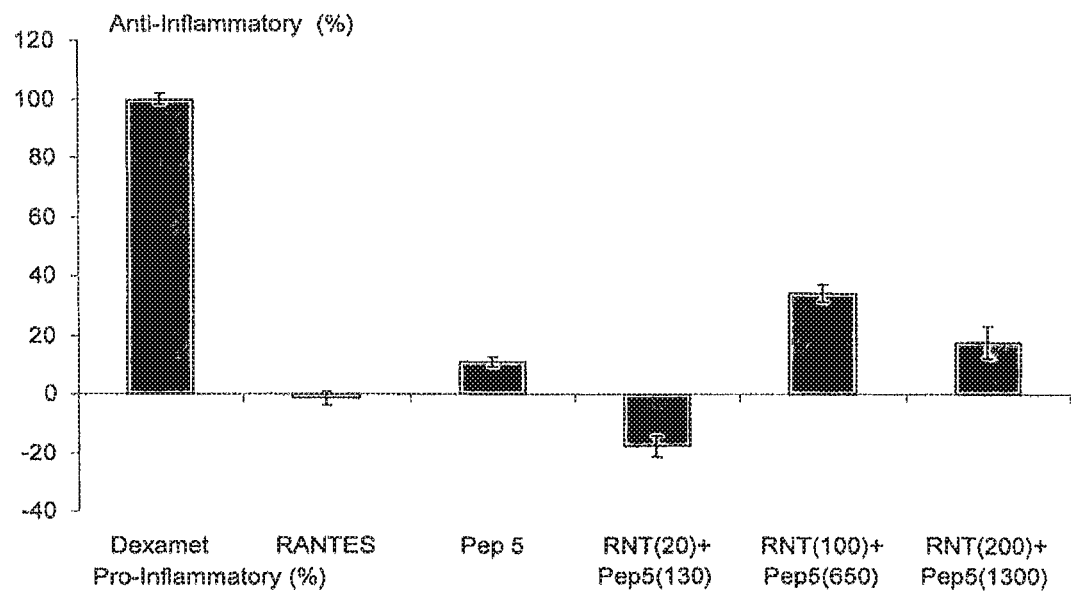
FIG. 17 shows the effect of CBP 5 combined with the CK, RANTES when administered to disease, DTH-induced mice.

Efficacy of the CK, RANTES (CCL5) and Peptide 5 and different doses of Peptide 5 combined with RANTES The CK RANTES, is expressed at elevated levels in inflammatory conditions and is classified as an inflammatory CK. As shown in FIG. 17, 200*ng* RANTES, administered to disease induced mice was slightly pro-inflammatory, increasing inflammation by <3% (<−3 in FIG. 17) compared with disease-induced, untreated animals. 1,300 ng Peptide 5 had an anti-inflammatory effect when administered to disease-induced mice, decreasing inflammation by 11% (11) compared with disease-induced, untreated animals. A combination of RANTES and Peptide 5 had a pro-inflammatory effect of 18% (−18) when administered to the disease-induced animals at a dose consisting of 20 ng RANTES and 130 ng Peptide 5. At a dose consisting of 100 ng RANTES and 550 ng Peptide 5, the anti-inflammatory effect of the combination was 34% (34), compared with disease-induced, untreated animals. At a dose consisting of 200 ng RANTES and 1300 ng Peptide 5, the anti-inflammatory effect was 18% (18). The molecular ratio of the respective doses was 1:50 (CK:Peptide). Given the pro-inflammatory-activity of RANTES alone and the anti-inflammatory activity of Peptide 5 by itself, the activities of the CK-Peptide combinations are evidence of formation of a RANTES-Peptide 5 complex and stability of the complex. At the sub-optimal dose (RANTES: 20 ng—Peptide 5 130 ng) the complex manifested pro-inflammatory activity, consistent with the biphasic properties of CKs. At low concentrations, CKs are chemo-attractants, inducing target (inflammatory) cell migration. At relatively high concentrations CKs inhibit target cell migration. An optimal dose (RANTES: 100 ng—Peptide 6: 550 ng) was required for a maximal anti-inflammatory effect, consistent with the biological activity of a competitive inhibitor of a disease related, wild type CK. At the supra-optimal dose, the active complex activated disease non-related CK receptors inducing a counter-indicative, pro-inflammatory response.

Figure 18:
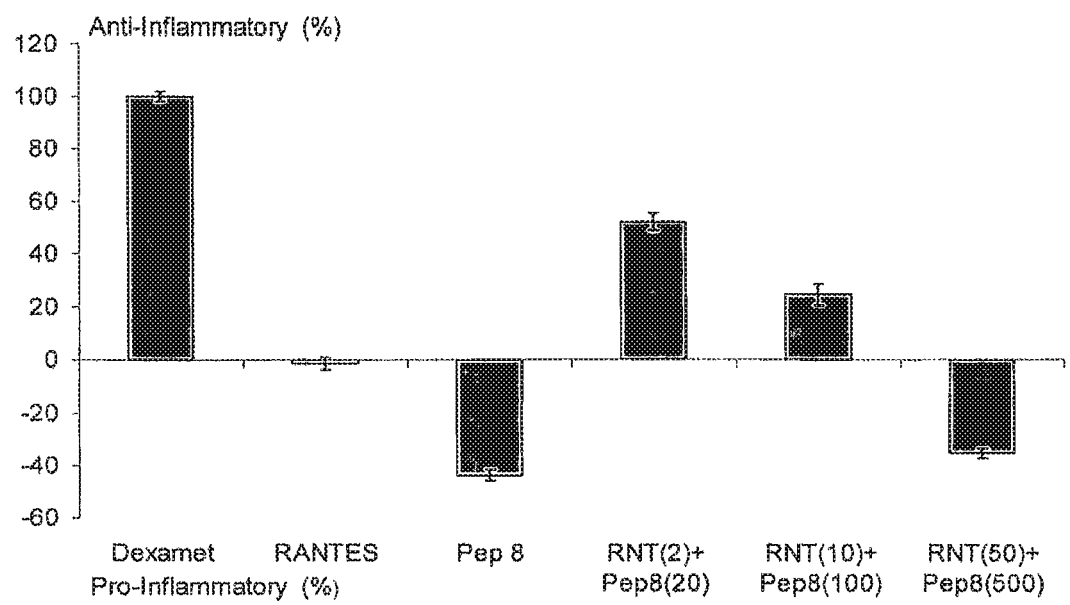
FIG. 18 shows the effect of CBP 8 combined with the CK, RANTES when administered to disease, DTH-induced mice.

Efficacy of the CK RANTES (CCL5), Peptide 8 and different doses of Peptide 8 combined with RANTES. Referring now to FIG. 18, as shown above, 200 ng of the CK RANTES when administered to disease induced mice is pro-inflammatory, increasing inflammation by <3% (<−3 in FIG. 18) compared with disease-induced, untreated animals. 1100 ng Peptide 8 had a pro-inflammatory effect when administered to disease-induced mice, increasing inflammation by 44% (−44) compared with disease-induced, untreated animals. A combination of RANTES and Peptide 8 had an anti-inflammatory effect when administered to the disease-induced animals at two doses, RANTES: 2 ng and Peptide 8: 20 ng (52% (52)) and RANTES: 10 ng and Peptide 8: 100 ng (25% (25)). With a dose of RANTES: 50 ng and Peptide 8: 500 ng, the pro-inflammatory effect was 36% (−36), compared with disease-induced, untreated animals. The molecular ratio of the respective doses was 1:50 (CK:Peptide). The pro-inflammatory activities of the individual components (RANTES and Peptide 8) and the anti-inflammatory activities of the CK-Peptide combinations are evidence of formation of a stable complex. Maximal anti-inflammatory activity was observed with combination consisting of RANTES: 2 ng and Peptide 8: 20 ng, consistent with the biological activity of a competitive inhibitor of a disease related, wild type CK. At the supra-optimal doses, the active complex activated disease non-related CK receptors inducing a counter-indicative, pro-inflammatory response.

Efficacy of the CK MCP1 (CCL2), Peptide 1 and Different Doses of Peptide 1 Combined with MCP1.

Figure 19:
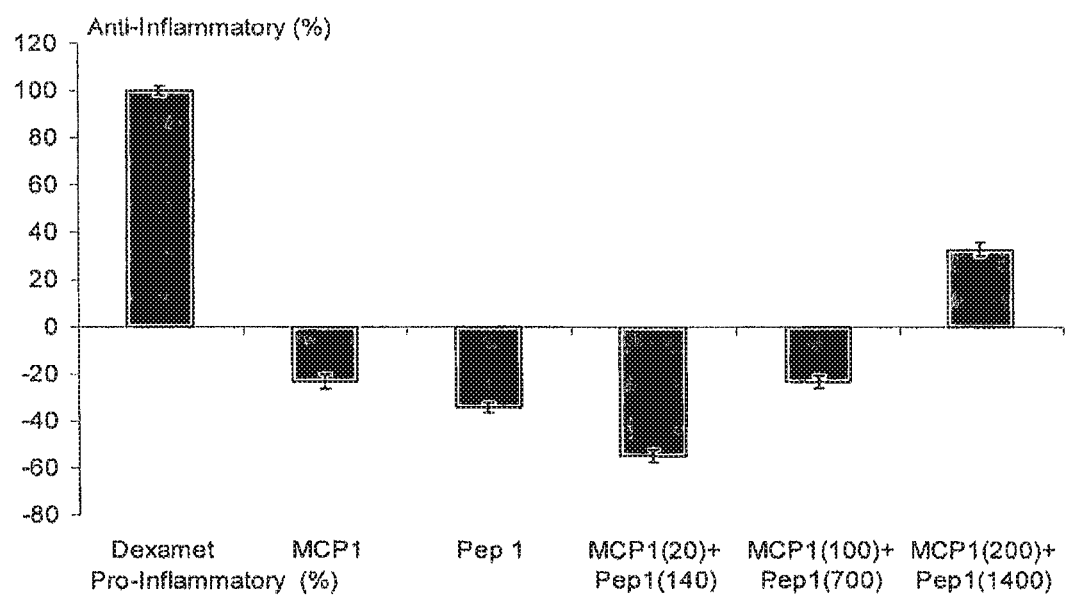
FIG. 19 shows the effect of CBP 1 combined with the CK, MCP-1 when administered to disease, DTH-induced mice.

The CK MCP1, is expressed at elevated levels in inflammatory conditions and is classified as an inflammatory CK. As shown in FIG. 19, 200 ng MCP1, administered to disease induced mice, was pro-inflammatory, increasing inflammation by 23% (−23 in FIG. 19) compared with disease-induced, untreated animals. 1,400 ng Peptide 1 had a pro-inflammatory effect when administered to disease-induced mice, increasing inflammation by 34% (−34) compared with disease-induced, untreated animals. A combination of MCP 1 and Peptide 1 had a pro-inflammatory effect when administered to the disease-induced animals at two doses, MCP1: 20 ng and Peptide 1: 140 ng (55% (55)) and MCP1: 100 ng and Peptide 1: 700 ng (23% (23)). At a dose of MCP1: 200 ng and Peptide 1: 1400 ng, the anti-inflammatory effect was 33% (33), compared with disease-induced, untreated animals. The molecular ratio of the respective doses was 1:50, CK: Peptide. The pro-inflammatory activities of the individual components (MIG and Peptide 1) and the anti-inflammatory activity of the CK-Peptide combination is evidence of formation of a stable complex. At the sub-optimal doses (MCP1: 20 ng—Peptide 1: 140 ng; MCP1: 100 ng—Peptide 1: 700 ng) the complex manifested pro-inflammatory activity, consistent with the biphasic properties of CKs. At low concentrations CKs are chemo-attractants, inducing target (inflammatory) cell migration. At relatively high concentrations CKs inhibit target cell migration. An optimal dose (MCP 1: 200 ng and Peptide 1: 1400 ng was required for the anti-inflammatory effect, consistent with the biological activity of a competitive inhibitor of a disease related, wild type CK.

Efficacy of the CK, MCP1 (CCL2), Peptide 5 and Different Doses of Peptide 5 Combined with MCP1.

Figure 20:
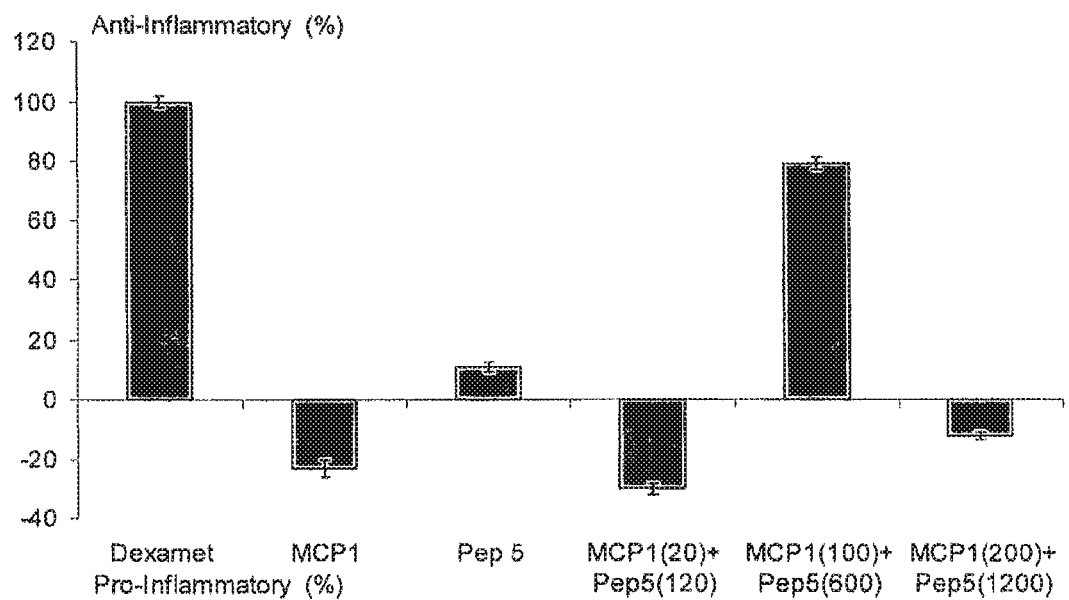
FIG. 20 shows the effect of CBP 5 combined with the CK, MCP-1 when administered to disease, DTH-induced mice.

The CK MCP1, is expressed at elevated levels in inflammatory conditions and is classified as an inflammatory CK. As shown in FIG. 20, 200 ng MCP1, administered to disease induced mice was pro-inflammatory, increasing inflammation by 23% (−23 in FIG. 20) compared with disease-induced, untreated animals. 1300 ng Peptide 5 had an anti-inflammatory effect when administered to disease-induced mice, decreasing inflammation by 11% (11) compared with disease-induced, untreated animals. A combination of MCP1 and Peptide 5 had a pro-inflammatory effect when administered to the disease-induced animals at two doses, MCP1: 20 ng and Peptide 5: 120 ng (23% (23)) and MCP1: 200 ng and Peptide 5: 1200 ng (11% (−11)). At a dose of MCP1: 100 ng and Peptide 5: 600 ng the anti-inflammatory effect was 79% (79), compared with disease-induced, untreated animals. The molecular ratio of the respective doses was 1:50, CK: Peptide. The pro-inflammatory activities of the individual components (MCP1 and Peptide 5) and the anti-inflammatory activity of the CK-Peptide combination is evidence of formation of a stable complex. At a sub-optimal dose (MCP 1: 20 ng—Peptide 5: 120 ng) the complex manifested pro-inflammatory activity, consistent with the biphasic properties of CKs. At low concentrations, CKs are chemo-attractants, inducing target (inflammatory) cell migration. At relatively high concentrations CKs inhibit target cell migration. An optimal dose (MCP1: 100 ng and Peptide 5: 600 ng) was required for the anti-inflammatory effect, consistent with the biological activity of a competitive inhibitor of a disease related, wild type CK. At the supra-optimal dose, the active complex activated disease non-related CK receptors inducing a counter-indicative, pro-inflammatory response.

Figure 21:
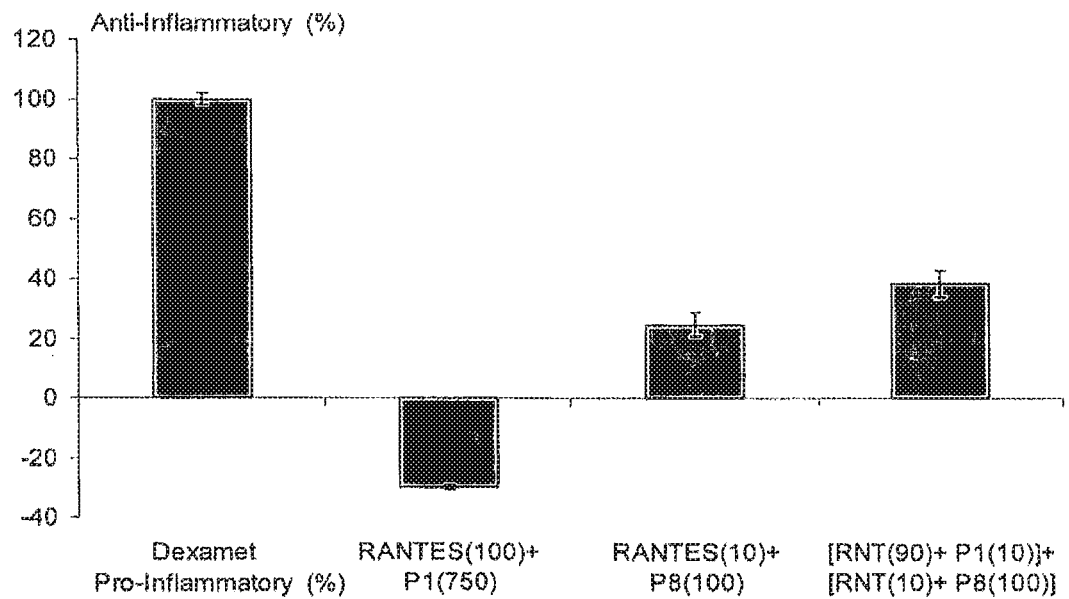
FIG. 21 shows the effect of CBP-CK combinations CBP 1-RANTES combined with CBP 8-RANTES when administered to disease, DTH-induced mice.

Efficacies of the CK-Peptide combinations, RANTES (CCL5)-Peptide 1 and RANTES-Peptide 8, separately and together. As shown in FIG. 21, a dose consisting of a combination of 100 ng RANTES and 750 ng Peptide 1, administered to disease induced mice, was pro-inflammatory, increasing inflammation by 30% (−30 in FIG. 21) compared with disease-induced, untreated animals. In contrast to this, a dose consisting of a combination of 10 ng RANTES and 100 ng Peptide 8 was anti-inflammatory, decreasing inflammation by 25% (25). The counter-indicative therapeutic activities of the respective RANTES-Peptide combinations, RANTES-Peptide 1 and RANTES-Peptide 8, was evidence that each of the peptides modulated RANTES activity in an opposite way and that each combination was a stable complex. The net effect of administrating RANTES-Peptide 1 together with RANTES-Peptide 8 to disease-induced animals (38% (38) anti-inflammatory) has implications for the pharmacological properties of the complexes. The net anti-inflammatory effect may be the consequence of competition between functionally discrete complexes for the same disease-related CK receptor or, alternatively, the result of activating functionally opposed, pro- and anti-inflammatory, receptors.

Efficacies of the CK-Peptide Combinations, IP10 (CXCL10)-Peptide 8 and RANTES (CCL5)-Peptide 8, Separately and Together.

Figure 22:
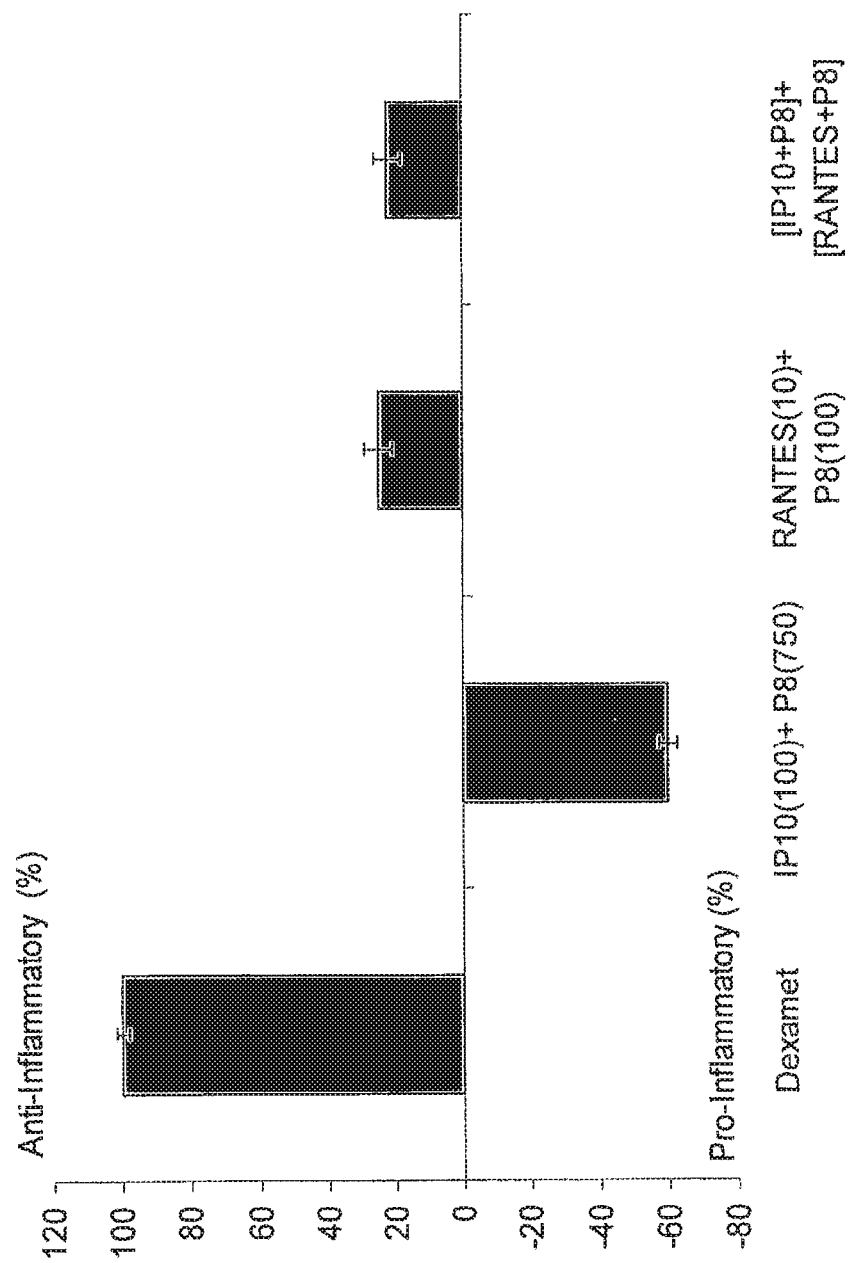
FIG. 22 shows the effect of the CBP-CK combinations, CBP 8-IP-10 combined with CBP 8-RANTES when administered to disease, DTH-induced mice.

A dose consisting of 100 ng IP10 and 750 ng Peptide 8, administered to the disease induced mice, was pro-inflammatory, increasing inflammation by 60% (−60 in FIG. 22) compared with disease-induced, untreated animals. A dose consisting of 10 ng RANTES and 100 ng Peptide 8 was anti-inflammatory, decreasing inflammation by 25% (25). The counter-indicative therapeutic activities of these two CK-Peptide combinations is evidence that Peptide 8 modulated the inflammatory CK IP10 and RANTES activities in opposite ways. The net anti-inflammatory effect may be the consequence of competition between functionally discrete complexes for the same disease-related CK receptor or, alternatively, the result of activating functionally opposed, pro- and anti-inflammatory, receptors.

Therapeutic Indications

Rheumatoid Arthritis:

Clinical observation and empirical evidence have indicated roles for RANTES, MIG, MCP-1 and IP10 and their respective cognate receptors, in the pathogenesis of Rheumatoid Arthritis. A combination consisting of RANTES and CBP 5 (see FIG. 17), RANTES and CBP 8 (see FIG. 18), MIG and CBP 8 (see FIG. 16), MCP-1 and CBP 1 (see FIG. 19), MCP1 and CBP 5 (see FIG. 20), or IP10 and CBP 8 (see FIG. 22), may be used in the treatment of rheumatoid arthritis.

Asthma:

The CKs, RANTES and MCP-1 and the CK receptors, CCR3, origin of CBP 1 and CBP 5 and CCR2, origin of CBP 8, are implicated in the pathogenesis of Asthma. A combination of RANTES and CBP 5 (see FIG. 17), RANTES and CBP 8 (see FIG. 18), MCP-1 and CBP 1 (see FIG. 19), or MCP-1 and CBP 5 (see FIG. 20), may be used in the treatment of Asthma.

Transplantation Rejection:

The levels of CKs, MIG, RANTES, MCP-1 and IP10 and the CK receptor, CCR2, origin of CBP 8, correlate with Organ Transplant Rejection. A combination of MIG and CBP 8 (see FIG. 16), RANTES and CBP 5 (see FIG. 17), RANTES and CBP 8 (see FIG. 18), MCP-1 and CBP 1 (see FIG. 19), MCP1 and CBP 5 (see FIG. 20), or IP10 and CBP 8 (see FIG. 22), may be used in the treatment of Transplant Rejection.

Multiple Sclerosis:

MIG, RANTES, MCP-1 and IP10 are Multiple Sclerosis-related CKs and the CK receptor, CCR2, origin of CBP 8, is implicated in the disease. A combination of MIG and CBP 8 (see FIG. 16), RANTES and CBP 5 (see FIG. 17), RANTES and CBP 8 (see FIG. 18), MCP-1 and CBP 1 (see FIG. 19), MCP1 and CBP 5 (see FIG. 20), or IP10 and CBP 8 (see FIG. 22), may be used in the treatment of Transplant Rejection.

Inflammatory Bowel Disease:

The CK, RANTES, is implicated in the pathogenesis of Inflammatory Bowel Disease. A combination of RANTES and CBP 5 (see FIG. 17), or RANTES and CBP 8 (see FIG. 18) may be used in the treatment of the disease.

Psoriasis:

The CKs, MIG and RANTES are implicated in the pathogenesis of Psoriasis. A combination of MIG and CBP 8 (see FIG. 16), RANTES and CBP 5 (see FIG. 17), or RANTES and CBP 8 (see FIG. 18), may be used in the treatment of the disease.

AIDS:

The cognate receptor of RANTES, CCR5, is involved in HIV infection and a validated drug target for the treatment of AIDS. A combination of RANTES and CBP 5 (see FIG. 17), or RANTES and CBP 8 (see FIG. 18), may be used as a competitive inhibitor of the virus in the treatment of the disease.

Cancer:

Metastasis and angiogenesis are essential for cancer pathogenesis. CKs mediate the cell migration of metastasis and the vascularization of angiogenisis. The CK-CBP combinations are potential modulators of and as such, therapeutic agents for, these pathogenic processes.

What is claimed:

1. A pharmaceutical composition comprising:
   (a) at least one complex formed between:
      (1) a cytokine selected from the group consisting of Growth-regulated protein alpha (GRO-α); Growth-regulated protein beta (GRO-β); Interleukin-8 Monokine induced by gamma interferon (MIG); Interferon gamma-(IL-8); induced protein 10 (IP-10); interferon-inducible T cell alpha chemoattractant (I-TAC); 1-309; Monocyte chemoattractant protein-1 (MCP-1); Monocyte chemoattractant protein-2 (MCP-2); Monocyte chemoattractant protein-4 (MCP-4); Macrophage inflammatory protein-1 (MIP-1); Macrophage inflammatory protein-1 alpha (MIP-1α); Regulated on activation, normal T cell expressed and secreted (RANTES); Eosinophil chemotactic protein (Eotaxin); Eosinophil chemotactic protein 2 (Eotaxin 2); Eosinophil chemotactic protein 3 (Eotaxin 3); Thymus and activation-regulated chemokine (TARC); Macrophage derived chemokine (MDC); Stromal cell-derived factor 1 alpha (SDF-1α); Stromal cell-derived factor 1 beta (SDF-1β); B-cell attracting chemokine-1 (BCA-1); Macrophage inflammatory protein-3 alpha (MIP-3α); Macrophage inflammatory protein-3 beta (MIP-3β); Exodus-2; Thymus-Expressed Chemokine (TECK); Cutaneous T cell-attracting chemokine (CTAC); Fractalkine; Lymphotactin; and Platelet factor-4 (PF-4); and
      (2) a peptide selected from the group consisting of SEQ ID No. 1, SEQ ID No. 6, SEQ ID No. 7, SEQ ID No. 8, SEQ ID No. 10, SEQ ID No. 11, and SEQ ID No. 12; and
   (b) a physiologically acceptable carrier wherein the peptide binds to the cytokine at greater than 25% of the Relative Fluorescence Units (RFU) range.

2. The pharmaceutical composition according to claim 1, in a form suitable for injection.

3. The pharmaceutical composition according to claim 1, wherein the cytokine is a chemokine.

4. The pharmaceutical composition according to claim 1, wherein the cytokine is an inflammatory cytokine.

5. The pharmaceutical composition according to claim 1, wherein the cytokine is a constitutive cytokine selected from the group consisting of:
   Thymus and activation-regulated chemokine (TARC);
   Macrophage derived chemokine (MDC);
   Stromal cell-derived factor 1 alpha (SDF-1α);
   Stromal cell-derived factor 1 beta SDF-1β;
   B-cell attracting chemokine-1 (BCA-1);
   Macrophage inflammatory protein-3 alpha (MIP-3α);
   Macrophage inflammatory protein-3 beta (MIP-3β);
   Exodus-2;
   Thymus-Expressed Chemokine (TECK); and
   Cutaneous T cell-attracting chemokine (CTAC).

6. The pharmaceutical composition according to claim 1, wherein the cytokine is a dual function cytokine.

7. The pharmaceutical composition according to claim 1, wherein the cytokine is selected from the group consisting of:
   (a) Growth-regulated protein alpha (GRO-α);
   (b) Growth-regulated protein beta (GRO-β);
   (c) Interleukin-8 (IL-8);
   (e) Monokine induced by gamma interferon (MIG);
   (9) Interferon gamma-induced protein 10 (IP-10);
   (h) interferon-inducible T cell alpha chemoattractant (I-TAC);
   (i) 1-309;
   (j) Monocyte chemoattractant protein-1 (MCP-1);
   (k) Monocyte chemoattractant protein-2 (MCP-2);
   (I) Monocyte chemoattractant protein-4 (MCP-4);
   (m) Macrophage inflammatory protein-1 (MIP-1);
   (n) Macrophage inflammatory protein-1 alpha (MIP-1α);
   (o) Regulated on activation, normal T cell expressed and secreted (RANTES);
   (P) Eosinophil chemotactic protein (Eotaxin);
   (q) Eosinophil chemotactic protein 2 (Eotaxin 2); and
   (r) Eosinophil chemotactic protein 3 (Eotaxin 3).

8. A method for treating an immune system disorder wherein the disorder involves delayed-type hypersensitivity reactions comprising administering to an individual in need of such treatment a pharmaceutical composition comprising:
   (a) at least one complex formed between:
      (1) a cytokine selected from the group consisting of Growth-regulated protein alpha (GRO-α); Growth-regulated protein beta (GRO-β); Interleukin-8 (IL-8); Monokine induced by gamma interferon (MIG); Interferon gamma- induced protein 10 (IP-10); interferon-inducible T cell alpha chemoattractant (I-TAC); 1-309; Monocyte chemoattractant protein-1 (MCP-1); Monocyte chemoattractant protein-2 (MCP-2); Monocyte chemoattractant protein-4 (MCP-4); Macrophage inflammatory protein-1 (MIP-1); Macrophage inflammatory protein-1 alpha (MIP-1α); Regulated on activation, normal T cell expressed and secreted (RANTES); Eosinophil chemotactic protein (Eotaxin); Eosinophil chemotactic protein 2 (Eotaxin 2); Eosinophil chemotactic protein 3 (Eotaxin 3); Thymus and activation-regulated chemokine (TARC); Macrophage derived chemokine (MDC); Stromal cell-derived factor 1 alpha (SDF-1α); Stromal cell-derived factor 1 beta (SDF-1β); B-cell attracting chemokine-1 (BCA-1); Macrophage inflammatory protein-3 alpha (MIP-3α); Macrophage inflammatory protein-3 beta (MIP-3β); Exodus-2; Thymus-Expressed Chemokine (TECK); Cutaneous T cell-attracting chemokine (CTAC); Fractalkine; Lymphotactin; and Platelet factor-4 (PF-4); and
      (2) a peptide selected from the group consisting of SEQ ID No. 1, SEQ ID No. 6, SEQ ID No. 7, SEQ ID No. 8, SEQ ID No. 10, SEQ ID No. 11, and SEQ ID No. 12; and (b) a physiologically acceptable carrier wherein the peptide binds to the cytokine at greater than 25% of the Relative Fluorescence Units (RFU) range.

9. The method according to claim 8, wherein the pharmaceutical composition is in a form suitable for injection.

10. The method according to claim 8, wherein the cytokine is a chemokine.

11. The method according to claim 8, wherein the cytokine is an inflammatory cytokine.

12. The method according to claim 8, wherein the cytokine is a constitutive cytokine selected from the group consisting of:
TARC;
MDC;
SDF-1α;
SDF-1β;
BCA-1;
MIP-3α;
MIP-3β;
Exodus-2;
TECK; and
CTAC.

13. The method according to claim 8, wherein the cytokine is selected from the group consisting of:
(a) GRO-α;
(b) GRO-β;
(c) NAP-2;
(d) IL-8;
(1) MIG;
(g) IP-10;
(h) 1-TAC;
(i) 1-309;
(j) MCP-1;
(k) MCP-2;
(l) MCP-4;
(m) MIP-1;
(n) MIP-1α;
(o) RANTES;
(p) Eotaxin;
(q) Eotaxin 2; and
(r) Eotaxin 3.

* * * * *

SEQUENCE LISTING

```
<160> NUMBER OF SEQ ID NOS: 13

<210> SEQ ID NO 1
<211> LENGTH: 8
<212> TYPE: PRT
<213> ORGANISM: Homo sapiens

<400> SEQUENCE: 1

Ser Tyr Tyr Asp Asp Val Gly Leu
1               5

<210> SEQ ID NO 2
<211> LENGTH: 9
<212> TYPE: PRT
<213> ORGANISM: Homo sapiens

<400> SEQUENCE: 2

Trp Val Phe Gly His Gly Met Cys Lys
1               5

<210> SEQ ID NO 3
<211> LENGTH: 7
<212> TYPE: PRT
<213> ORGANISM: Homo sapiens

<400> SEQUENCE: 3

Leu Phe Gly Asn Asp Cys Glu
1               5

<210> SEQ ID NO 4
<211> LENGTH: 9
<212> TYPE: PRT
<213> ORGANISM: Homo sapiens

<400> SEQUENCE: 4

Trp Val Phe Gly Thr Phe Leu Cys Lys
1               5

<210> SEQ ID NO 5
<211> LENGTH: 9
<212> TYPE: PRT
<213> ORGANISM: Homo sapiens

<400> SEQUENCE: 5

Trp Val Phe Gly Asn Ala Met Cys Lys
1               5

<210> SEQ ID NO 6
<211> LENGTH: 7
```

```
<212> TYPE: PRT
<213> ORGANISM: Homo sapiens

<400> SEQUENCE: 6

Phe Phe Gly Leu Asn Asn Cys
1               5

<210> SEQ ID NO 7
<211> LENGTH: 9
<212> TYPE: PRT
<213> ORGANISM: Homo sapiens

<400> SEQUENCE: 7

Thr Thr Phe Phe Asp Tyr Asp Tyr Gly
1               5

<210> SEQ ID NO 8
<211> LENGTH: 5
<212> TYPE: PRT
<213> ORGANISM: Homo sapiens

<400> SEQUENCE: 8

Glu Asp Ser Val Tyr
1               5

<210> SEQ ID NO 9
<211> LENGTH: 9
<212> TYPE: PRT
<213> ORGANISM: Homo sapiens

<400> SEQUENCE: 9

Trp Val Phe Gly Ser Gly Leu Cys Lys
1               5

<210> SEQ ID NO 10
<211> LENGTH: 9
<212> TYPE: PRT
<213> ORGANISM: Homo sapiens

<400> SEQUENCE: 10

His His Thr Cys Ser Leu His Phe Pro
1               5

<210> SEQ ID NO 11
<211> LENGTH: 9
<212> TYPE: PRT
<213> ORGANISM: Homo sapiens

<400> SEQUENCE: 11

His Tyr Thr Cys Ser Ser His Phe Pro
1               5

<210> SEQ ID NO 12
<211> LENGTH: 10
<212> TYPE: PRT
<213> ORGANISM: Homo sapiens

<400> SEQUENCE: 12

Asp Arg Tyr Leu Asn Ile Val His Ala Thr
1               5                   10

<210> SEQ ID NO 13
<211> LENGTH: 6
<212> TYPE: PRT
<213> ORGANISM: Homo sapiens
```

<400> SEQUENCE: 13

Thr Lys Cys Gln Lys Glu
1               5